(12) United States Patent
Haaf et al.

(10) Patent No.: US 6,391,564 B1
(45) Date of Patent: May 21, 2002

(54) METHODS AND COMPOSITIONS UTILIZING RAD51

(75) Inventors: Thomas Haaf, Berlin (DE); Efim Ilya Golub, New Haven, CT (US); Gurucharan Reddy, Redwood City, CA (US); Charles Meyer Radding, Hamden; David C. Ward, Madison, both of CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/179,916

(22) Filed: Oct. 27, 1998

Related U.S. Application Data

(62) Division of application No. 09/007,020, filed on Jan. 14, 1998, now Pat. No. 6,090,539.
(60) Provisional application No. 60/045,668, filed on May 6, 1997, and provisional application No. 60/035,834, filed on Jan. 30, 1999.

(51) Int. Cl.$^7$ ................. G01N 33/53; G01N 33/566; C07K 16/00
(52) U.S. Cl. ................. 435/7.1; 436/501; 530/387.1
(58) Field of Search ................. 435/7.1; 436/501; 530/387.1

(56) References Cited

FOREIGN PATENT DOCUMENTS

WO          98/20030          5/1998

OTHER PUBLICATIONS

Peter et al. Advances in apoptosis research. 12736–12737. vol. 94. Nov. 1997.*

Haaf et al. Nuclear foci of mamalian Rad51 recombination protein in somatic cells after DNA damage and its localization in synaptonemal complexes. Proc. Natl. Acad. Sci. USA vol. 92 pp. 2298–2302, 1995.*

Hunter Cooperation between Oncogenes. Cell. vol. 64 pp. 249–270, 1991.*

Chanet et al., "Semidominant Mutations in the Yeast Rad51 Protein and Their Relationships with the Srs2 Helicase," *Molecular and Cellular Biology,* 16(9):4782–4789 (Sep. 1996).

Stürzbecher et al., "P53 Is Linked Directly to Homologous Recombination Processes via Rad51/reca Protein Interaction," *EMBO Journal,* 15(8)1992–2002 (1996).

Sharan et al., "Embryonic Lethality and Radiation Hypersensitivity Mediated by Rad51 in Mice Lacking Brca2," *Nature,* 386:804–810 (Apr. 1997).

Hayes et al. "Complex Formation in Yeast Double–Strand Break Repair: Participation of Rad51, Rad52, Rad55 and Rad57 Proteins," *Proc. Natl. Acad. Sci. USA,* 92:6925–6929 (1995).

Benson et al., "Purification and Characterization of the Human Rad51 Protein, an Analogue of E. Coli RecA.," *EMBO J.,* 13:5764–5771 (1994).

Haaf, et al., "Nuclear Foci of Mammalian RAD51 Recombination Protein in Somatic Cells After DNA Damage and its Localization in Synaptonemal Complexes," *Proc. Natl. Acad. Sci. USA,* 92:2298–2302 (Mar. 1995).

* cited by examiner

*Primary Examiner*—John S. Brusca
(74) *Attorney, Agent, or Firm*—Flehr Hohbach Test Albritton & Herbert LLP; Richard F. Trecartin, P.C.

(57) ABSTRACT

Compositions and methods are provided for identifying and diagnosing individuals at risk for a disease state associated with aberrant Rad41 foci.

18 Claims, 6 Drawing Sheets

(6 of 6 Drawing Sheet(s) Filed in Color)

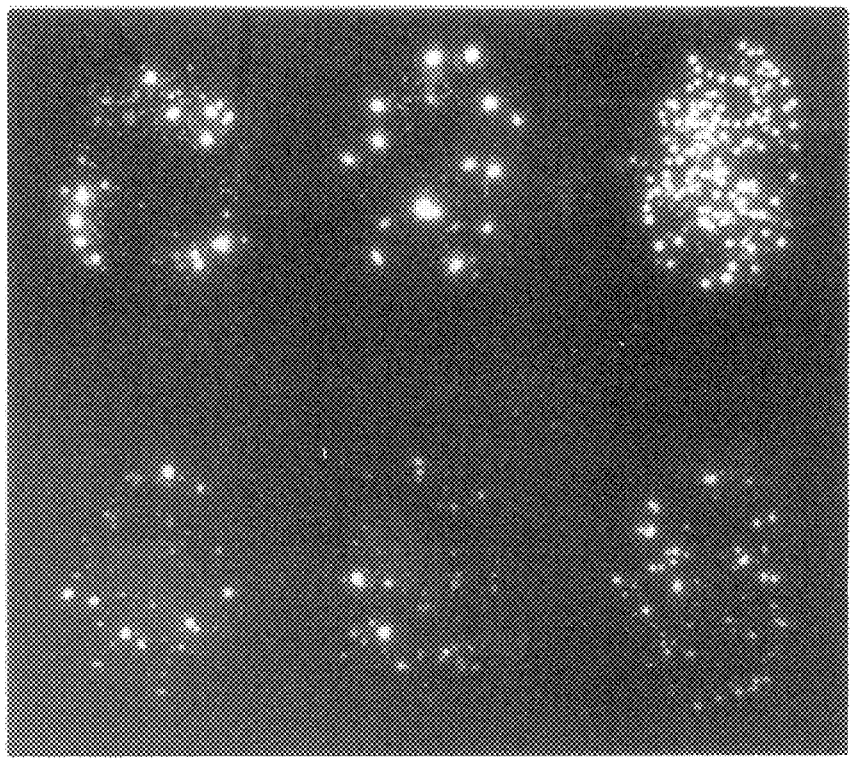
FIG._1
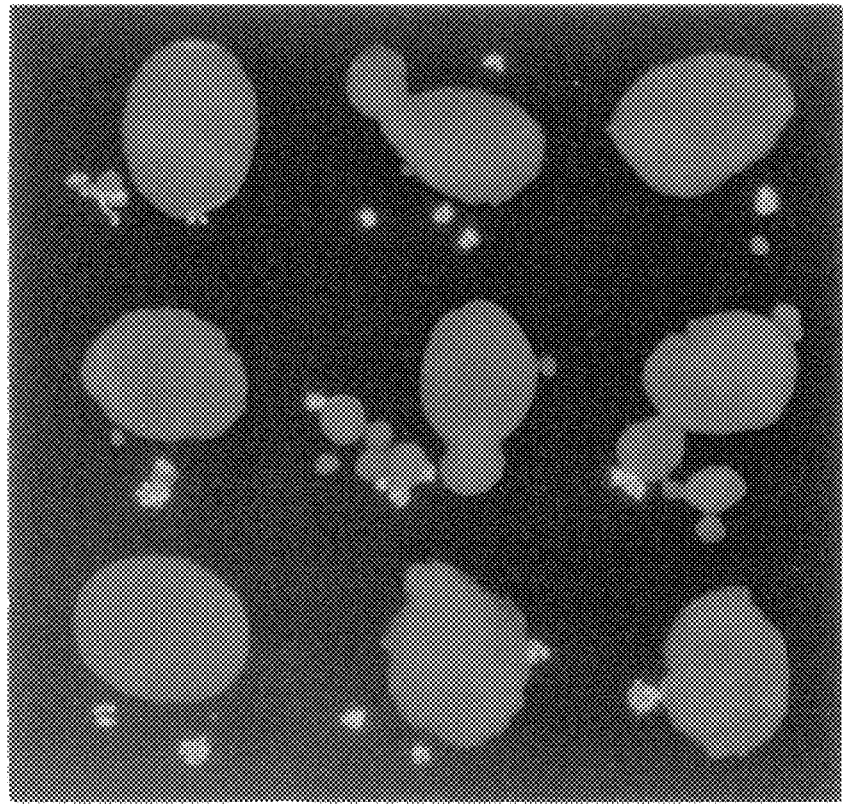
FIG._4

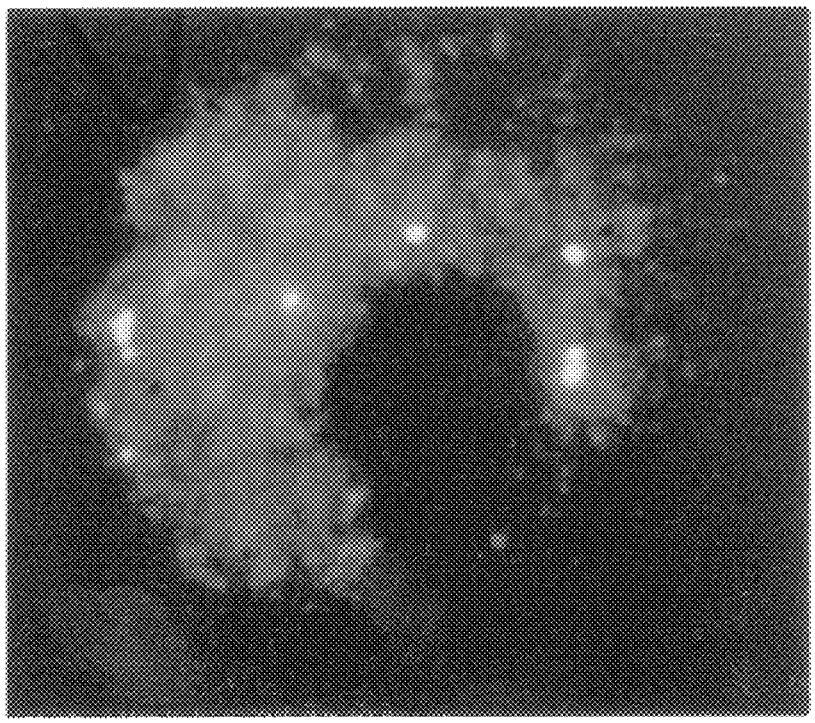
FIG._2A
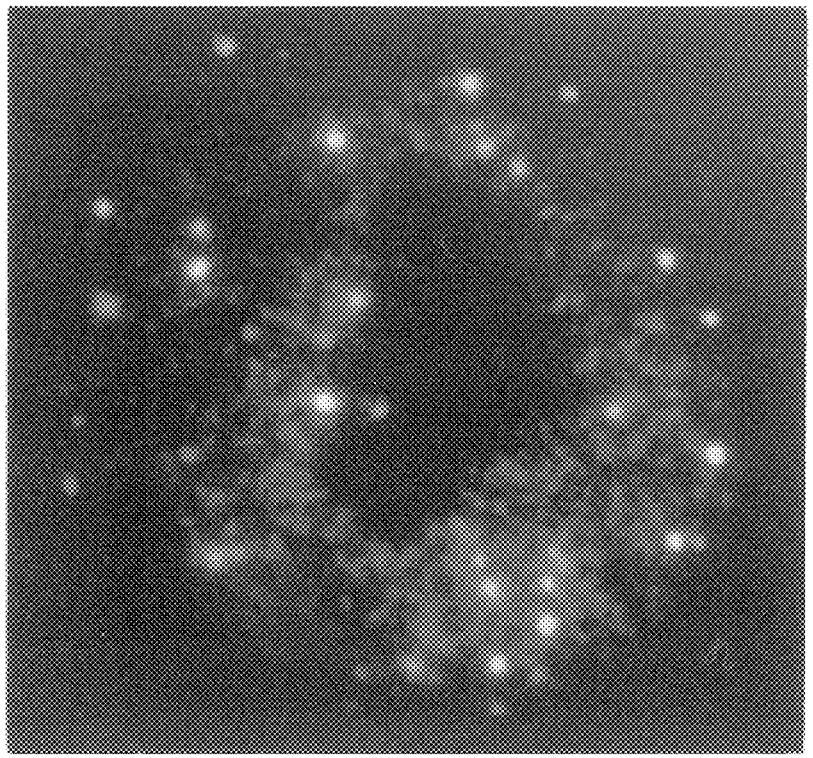
FIG._2B

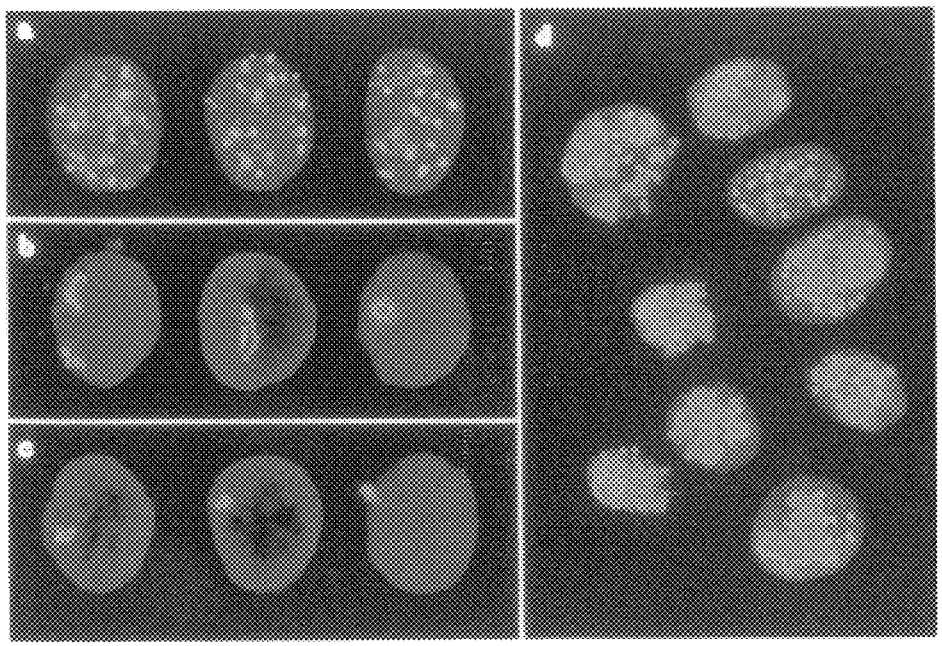
FIG._3A
FIG._3B
FIG._3C
FIG._3D

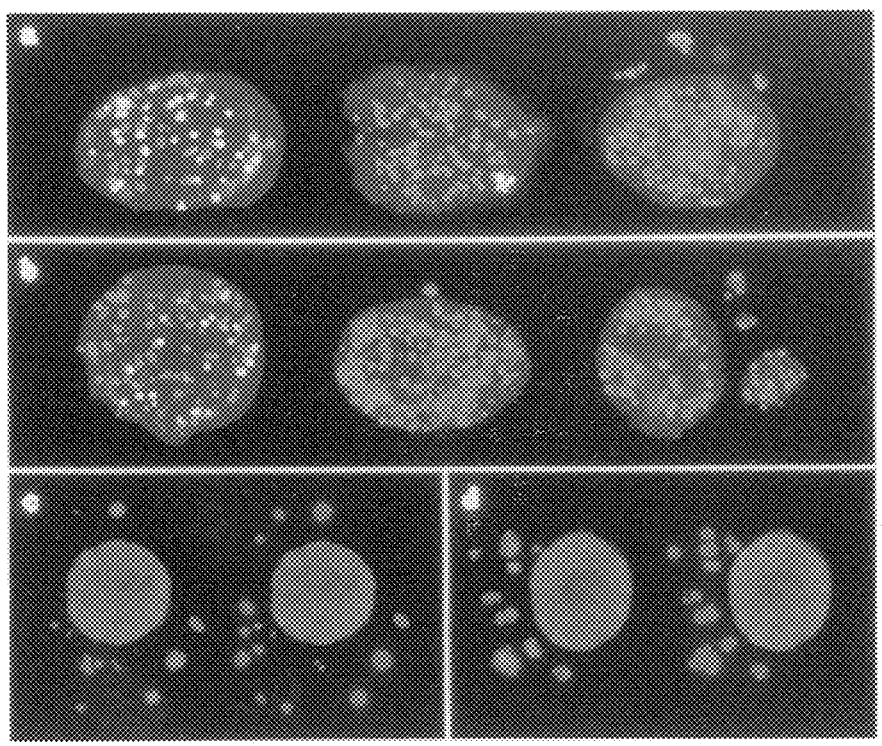
FIG._5A
FIG._5B
FIG._5C  FIG._5D

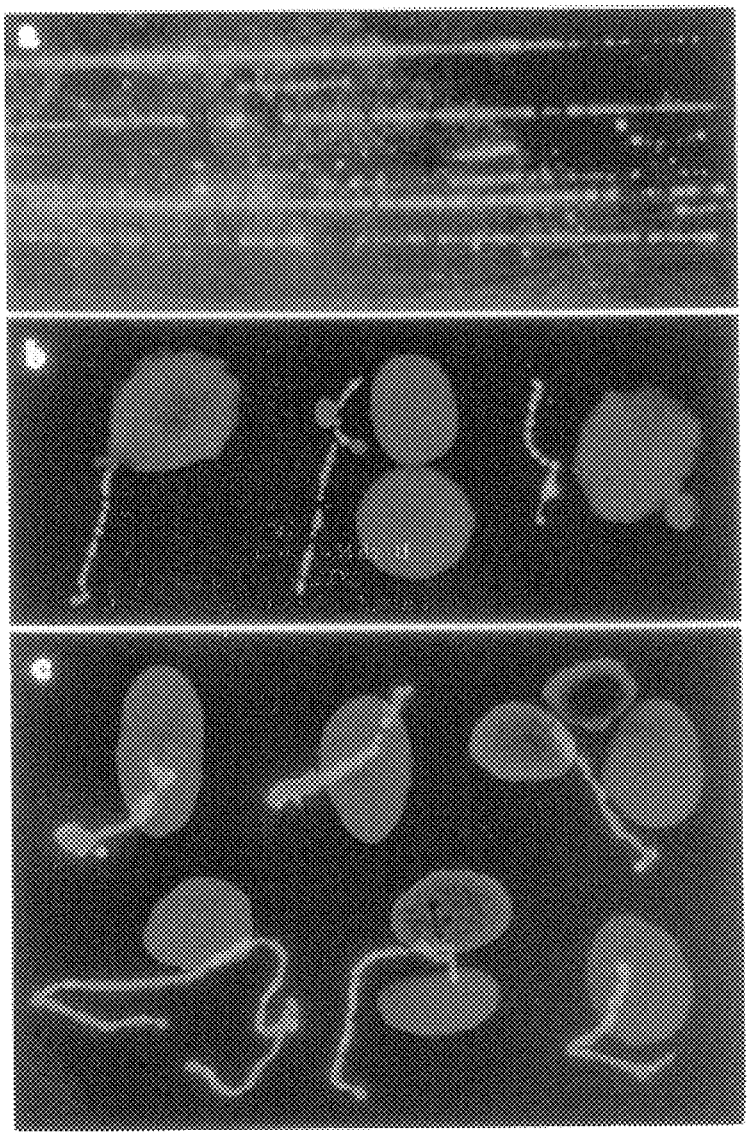
FIG._6A
FIG._6B
FIG._6C

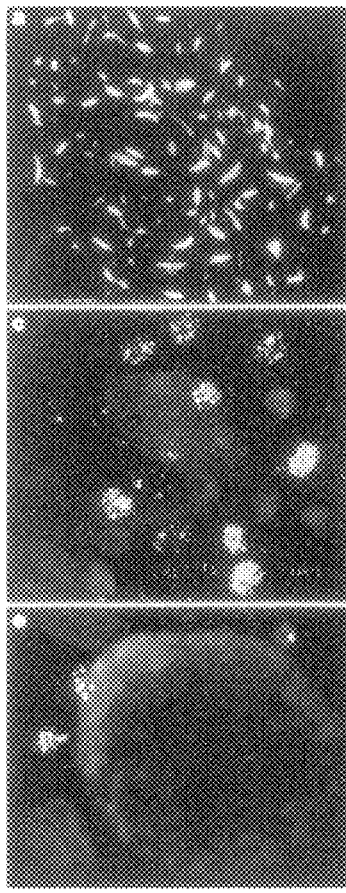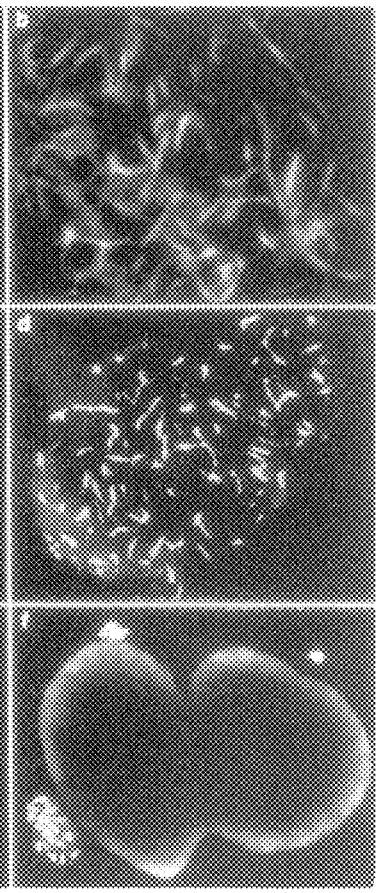
FIG._7A  FIG._7B
FIG._7C  FIG._7D
FIG._7E  FIG._7F

METHODS AND COMPOSITIONS UTILIZING RAD51

This application is a divisional of U.S. Ser. No. 09/007,020, filed Jan. 14, 1998, U.S. Pat. Ser. No. 6,090,539 which claims the benefit of U.S. Provisional Application Number 60/035,834, filed Jan. 30, 1997 and Ser. No. 60/045,668, filed May 6, 1997, all of which are expressly incorporated herein.

FIELD OF THE INVENTION

The invention relates to methods of diagnosis and screening utilizing Rad51 molecules.

BACKGROUND OF THE INVENTION

Homologous recombination is a fundamental process which is important for creating genetic diversity and for maintaining genome integrity. In *E. coli* RecA protein plays a central role in homologous genetic recombination in vivo and promotes homologous pairing of double-stranded DNA with single-stranded DNA or partially single-stranded DNA molecules in vitro. Radding, C. M. (1988). Homologous pairing and strand exchange promoted by Escherichia coli RecA protein. Genetic Recombination. Washington, American Society for Microbiology. 193–230; Radding, C. M. (1991). J. Biol. Chem. 266: 5355–5358; Kowalczykowski, et al., (1994). Annu. Rev. Biochem. 63: 991–1043. In the yeast *Saccharomyces cerevisiae* there are several genes with homology to recA gene; Rad51, Rad57 and Dmc1. Rad51 is a member of the Rad52 epistasis group, which includes Rad50, Rad51, Rad52, Rad54, Rad55 and Rad57. These genes were initially identified as being defective in the repair of damaged DNA caused by ionizing radiation and were subsequently shown to be deficient in both genetic recombination and the recombinational repair of DNA lesions. Game, J. C. (1983). Yeast Genetics: Fundamental and applied aspects. J. F. T. Spencer, D. H. Spencer and A. R. W. Smith, eds (New-York:Springer-Verlag): 109–137; Haynes, et al., (1981). The molecular biology of the yeast Saccharomyces cerevisiae: Life cycle and inheritance. J. N. Strathem, E. W. Jones and J. M. Broach, eds (Cold Spring harbor, New York:Cold Spring Harbor laboratory press): 371–414; Resnick, M. A. (1987). Meiosis, P. B. Moens, ed. (New York: Academic Press) : 157–210. During meiosis Rad51 mutants accumulate DNA double-strand breaks at recombination hot spots (Shinohara, et al., (1992). Cell 69: 457–470). Yeast rad51 gene was cloned and sequenced (Basile, et al., (1992). Mol. Cell. Biol. 12: 3235–3246; Aboussekhara, et al., (1992) Mol. Cell. Biol. 12: 3224–3234). Although yeast Rad51 gene shared homology with *E. coli* recA gene, the extent of homology was not very strong (27%). However, the extent of structural conservation between RecA protein and Rad51 protein became apparent when the yeast Rad51 protein was isolated and was shown to form nucleoprotein filaments that were almost identical to the nucleoprotein filaments formed by RecA protein (Ogawa, et al., (1993). CSH Symp. Quant. Biol. 58: 567–576; Ogawa, T., et al., (1993). Science 259: 1896–1899; Story, et al., (1993). Science 259: 1892–1896). Recently genes homologous to *E. coli* recA and yeast Rad51 were isolated from all groups of eukaryotes, including mammals (Morita, et al., (1993). Proc. Natl. Acad. Sci. USA 90, 6577–6580; Shinohara, et al., (1993). Nature Genet. 4, 239–243; Heyer, W. D. (1994). Experientia 50, 223–233; Maeshima, et al., (1995). Gene 160: 195–200). Phylogenetic analysis by Ogawa and co workers suggested the existence of two sub-families within eukaryotic RecA homologs: the Rad51-like (Rad51 of human, mouse, chicken, S. cerevisiae, S. pombe and Mei3 of Neurospora crassa) and the Dmc1-like genes (S. cerevisiae Dmc1 and Lilium longiflorum LIM15) (Ogawa, supra). All these Rad51 genes share significant homology with residues 33–240 of the *E. coli* RecA protein, which have been identified as a 'homologous core' region.

Yeast and human Rad51 proteins have been purified and characterized biochemically. Like *E. coli* RecA protein, yeast and human Rad51 protein polymerizes on single-stranded DNA to form a right-handed helical nucleoprotein filament which extends DNA by 1.5 times (Story, supra; Benson, et al., (1994) EMBO J. 13, 5764–5771). Moreover like RecA protein Rad51 protein promotes homologous pairing and strand exchange in an ATP dependent reaction (Sung, P. (1994). Science 265, 1241–1243; Sung, P. and D. L. Robberson (1995). Cell 82: 453–461; Baumann, et al., (1996) Cell 87, 57–766; Gupta, et al., (1997) Proc. Natl. Acad. Sci. USA 94, 463–468). Surprisingly, polarity of strand exchange performed by Rad51 protein is opposite to that of RecA protein (Sung and Robberson supra) and the relevance of this observation remains to be seen.

Surprisingly, studies with mouse models show that targeted disruption of the Rad51 gene leads to an embryonic lethal phenotype (Tsuzuki, et al., (1996). Proc. Natl. Acad. Sci. USA 93: 6236–6240). Moreover attempts to generate homozygous Rad51-/-embryonic stem cells have not been successful. These results show that Rad51 plays an essential role in cell proliferation, a surprise in view of the viability of S.cerevisiae carrying Rad51 deletions. It is also interesting to note that Rad51 was found to be associated with RNA polymerase II transcription complex (Maldonado, et al., (1996). Nature 381, 86–89), the specificity and functional nature of these interactions remains to be seen but all these observations point to a pleiotropic role of hsRad51 in DNA metabolism.

While Rad51 transcripts and protein are present in all the cell types examined thus far, the highest transcript levels are found in tissues active in recombination, including spleen, thymus, ovary and testis (Morita, supra). Rad51 is specifically induced in murine B cells cultured with lipopolysaccharide, which stimulates switch recombination and Rad51 localizes to nuclei of switching B cells (Li, et al., (1996). Proc. Natl. Acad. Sci. USA 93: 10222–10227). These findings are consistent with the view that Rad51 plays an important role in lymphoid specific recombination events such as V(D)J recombination and immunoglobulin heavy chain class switching. In spermatocytes undergoing meiosis, Rad51 is enriched in the synaptonemal complexes, which join paired homologous chromosomes (Haaf, et al., (1995) Proc. Natl. Acad. Sci. USA 92, 2298–2302; Ashley, et al., (1995) Chromosoma 104: 19–28; Plug, et al., (1996). Proc. Natl. Acad. Sci. USA 93: 5920–5924). In cultured human cells, Rad51 protein is detected in multiple discrete foci in the nucleoplasm of a few cells by immunofluorescent antibodies. After DNA damage, the localization of Rad51 changes dramatically when multiple foci form in the nucleus and stain vividly with anti-Rad51 antibodies (Haaf, supra, 1995). After DNA damage the percentage of cells with focally concentrated Rad51 protein increases; the same cells show unscheduled DNA-repair synthesis.

Micronuclei (MN) originate from chromosomal material that is not incorporated into daughter nuclei during cell division. Different chemicals and treatment of cells induce qualitatively different types of micronuclei. NW caused by ionizing radiation or clastogens (i.e. 5-azacytidine) mostly contain acentric chromosome fragments (Verhaegen, F., and Vral, A. (1994). Radiation Res. 139, 208–213; Stopper, et al., (1995). Carcinogenesis 16, 1647–1650). In contrast, MN induced by ancuploidogens (i.e. colcemid) result from lagging whole chromosomes and stain positively for the presence of kinetochores/ centromeres (Marrazini et al., 1994; Stopper, et al., (1994). Mutagenesis 9, 411–416). Determination of MN frequencies represents a good assay to measure genetic damage in cells, since it is much faster and simpler than karyotype analyses. In this light, the MN test has been widely used as a dosimeter of human exposure to radiation or clastogenic and aneugenic chemicals, and for the detection and risk assessment of environmental mutagens and carcinogens (Heddle, et al., (1991) Environmental Mol. Mutagenesis 18, 277–291; Norppa, et al., (1993). Environmental Health Perspect. 101, Supp. 3, 139–143; Hahnfeldt, et al., (1994) Radiation Res. 138, 239–245). However, although the MN assay is a convenient in situ method to monitor cytogenetic effects, the understanding of the connection between initial DNA damage and formation of MN is still poor.

The tumor suppressor p53 prevents tumor formation after DNA damage by halting cell cycle progression to allow DNA repair or by inducing apoptotic cell death. Loss of wild-type p53 function renders cells resistant to DNA damage induced cell cycle arrest and ultimately leads to genomic instabilities including gene amplifications, translocations and aneuploidy. Some of these chromosomal lesions are based on mechanisms that involve recombinational events (Lane, D. P. (1992). Nature 358: 15–16; Lane, D. P. (1993). Nature 362: 786–787; Sturzbecher, et al., (1996). EMBO J. 15: 1992–2002) reported that wild-type tumor suppressor protein p53 interacts physically with human Rad51 protein and it inhibits the biochemical functions of Rad51 like ATPase and strand exchange. In vivo temperature sensitive mutant p53 formed complexes with Rad51 only in wild type but not in mutant conformation. They suggested that gene amplifications and other types of chromosome rearrangements involved in tumour progression might occur not only as a result of inappropriate cell proliferation but as a direct consequence of a defect in p53 mediated control of homologous recombination processes due to mutations in the p53 gene. (Meyn, et al., (1994). Int. J. Radiat. Biol. 66: S141-S149) showed that normal cells transfected with a dominant-negative p53 mutant acquired interference with the G1-S cell cycle checkpoint and showed up to an 80-fold elevation in RAD51 mediated homologous DNA recombination rates compared with the normal parental control cells. Thus, loss of normal p53 function may cause a loss in control of normal DNA repair, recombination, and ultimately replication, resulting in inappropriate cell division and neoplastic growth. Breast tumour cells have mutated p53 genes and proteins and have various types of chromosomal aberrations like insertions, deletions, rearrangements, amplifications etc., indicative of abnormally controlled recombination.

Accordingly, it is an object of the invention to provides methods of diagnosis and screening which focus on Rad51.

SUMMARY OF THE INVENTION

In accordance with the objects outlined above, the present invention provides methods of diagnosing individuals at risk for a disease state which results in aberrant Rad51 loci. The methods comprise determining the distribution of Rad51 foci in a first tissue type of a first individual, and then comparing the distribution to the distribution of Rad51 foci from a second normal tissue type from the first individual or a second unaffected individual. A difference in the distributions indicates that the first individual is at risk for a disease state which results in aberrant Rad51 loci. Preferred disease states include cancer and disease states associated with apoptosis.

In an additional aspect, the present invention provides methods for identifying apoptotic cells and cells under stress associated with nucleic acid modification. The methods comprise determining the distribution of Rad51 foci in a first cell, and comparing the distribution to the distribution of Rad51 foci from a second non-apoptotic cell. A difference in the distributions indicates that the first cell is apoptotic or under stress.

In a further aspect, the present invention provides methods for identifying a cell containing a mutant Rad51 gene comprising determining the sequence of all or part of at least one of the endogenous Rad51 genes.

In an additional aspect, the invention provides methods of identifying the Rad51 genotype of an individual comprising determining all or part of the sequence of at least one Rad51 gene of the individual. The method may include comparing the sequence of the Rad51 gene to a known Rad51 gene.

In a further aspect, the present invention provides methods for screening for a bioactive agent capable of binding to Rad51. The methods comprise adding a candidate bioactive agent to a sample of Rad51, and determining the binding of the candidate agent to the Rad51 .

In an additional aspect, the invention provides methods for screening for a bioactive agent capable of modulating the activity of Rad51. The method comprises the steps of adding a candidate bioactive agent to a sample of Rad51, and determining an alteration in the biological activity of Rad51. The method may also comprise adding a candidate bioactive agent to a cell, and determining the effect on the formation or distribution of Rad51 foci in the cell.

In a further aspect, the invention provides methods of inducing apoptosis in a cell comprising increasing the activity of Rad51 in the cell. This can be done by overexpressing an endogenous Rad51 gene, or by administration of a gene encoding Rad51 or the protein itself.

In an additional aspect, the present invention provides composition comprising a nucleic acid encoding a Rad51 protein, and a nucleic acid encoding a tumor suppressor protein. The tumor suppressor protein may be p53 or a BRCA protein.

BRIEF DESCRIPTION OF THE DRAWINGS

This patent or application file contains at least one drawing executed in color. Copies of this patent or patent application with color drawing(s) will be provided by the Patent and Trademark Office upon request and payment of the necessary fee.

FIG. 1 is a digital image of photographs of cells that depict type I and type II Rad51 foci, respectively.

FIGS. 2A and 2B are digital images of photographs of two different breast cancer cells from a breast cancer cell line (BT20) that show Rad51 foci. The staining is localized to the nucleus, and does not occur in either the cytoplasm or the nucleolus.

FIGS. 3A, 3B, 3C and 3D show dynamic changes in the higher-order nuclear organization of Rad51 foci after DNA damage and cell-cycle arrest. (a–c) TGR-1 fibroblasts were irradiated with a lethal dose (900 rad) of $^{137}$Cs and then allowed to recover for various times. Rad51 protein is stained (light), nuclei are counterstained with DAPI. Three hours after irradiation (a), Rad51 foci are distributed throughout the entire nuclear volume. Many foci have a double-dot appearance. After 16 hrs (b), clusters of Rad51 foci and linear higher-order structures are formed. Somatic pairing of linear strings of Rad51 foci is observed. After 30 hrs (c), Rad51 clusters move towards the nuclear periphery and are eliminated into micronuclei. (d) Simultaneous staining of Rad51 protein (light) and replicating DNA (dark) in an exponentially growing, XPA fibroblast culture. BrdU was incorporated into DNA for 30 hrs and detected with red anti-BrdU antibody. Note that the Rad51-positive cell is devoid of BrdU label. Magnification 1000×.

FIG. 4 depicts the exclusion of Rad51-protein in micronuclei after DNA damage. TGR-1 fibroblasts, two days after $^{137}$Cs irradiation with a dose of 900 rad. Rad51 protein is stained by (light), nuclei are counterstained with DAPI. Note the complete absence of Rad51-protein staining in nuclei. All Rad51 foci are excluded into micronuclei. Most micronuclei exhibit paired Rad51-protein structures. Magnification 1000×.

FIGS. 5A, 5B, 5C and 5D illustrates that apoptotic bodies (micronuclei) contain Rad51 protein and fragmented DNA. (a and b) TGR-I nuclei, 3 hrs (right), 16 hrs (middle), and 30 hrs (left) after $^{137}$Cs irradiation. Rad51-protein foci show light staining. The repair proteins Rad52 (a) and Gadd45 (b) are detected by antibody probes (darker staining). Nuclei are counterstained with DAPI. Note that neither Rad52 nor Gadd45 foci co-localize with Rad51 . Only the Rad51 foci segregate into micronuclei. (c and d) Micronuclei induced by treatment of TGR-1 cultures with colcemid (c) and etoposide (d) contain Rad51 protein (light staining, left nucleus) and fragmented DNA (darker staining, right nucleus). Magnification 1000×.

FIGS. 6A, 6B and 6C show the association of Rad51 protein with linear DNA molecules. (a) Mechanically stretched chromatin prepared from a $^{137}$Cs-irradiated cell culture and stained with light anti-HsRad51 antibodies. The Rad51 signals appear as beads-on-a-string on the linearly extended chromatin fibers. (b and c) DNA fibers excluded from TGR-1 nuclei, one day after $^{137}$Cs irradiation. Preparations are not experimentally stretched. Chromatin is counterstained with DAPI. The DNA fibers are covered with Rad51 protein (c, light staining), whereas the remaining nuclei are devoid of detectable Rad51 foci. DNA-strand breaks in chromatin fibers are end labeled with fluorescent nucleotides (c, darker staining colocalizing with the Rad51 staining). Some fibers appear to form micronuclei. Magnification 1000×.

FIGS. 7A, 7B, 7C, 7D, 7E and 7F show the linear higher-order structures of Rad51 protein in overexpressing nuclei and in colcemid-induced micronuclei. Rad51 protein is stained with anti-Rad51 antiserum, detected by green FITC fluorescence (light staining). Preparations are counterstained with DAPI, except the nucleus in b. (a and b) Human 710 kidney cells overexpressing Rad51 fused to a T1-tag epitope.

Nuclei are filled with a network of linear Rad51 structures. Magnification 1000×. (c) Subconfluent rat TGR 928.1–9 cells overexpressing HsRad51. Nuclear staining is most prominent in cells during $G_0$ and $G_1$ phase of the cell cycle. Magnification 1000×. (d) TGR 928.1–9 nucleus filled with linear Rad51 structures. Magnification 1000×. (e and f) Linear Rad51 structures in colcernid-induced micronuclei. TGR-1 fibroblasts were treated with colcemid for one day and then allowed to recover for two days. Note the absence of Rad51 staining in the nuclei. Magnification 1 000×.

DETAILED DESCRIPTION OF THE INVENTION

The present invention is directed to a series of discoveries relating to the pivotal role that Rad51 plays in a number of cellular functions, including those involved in disease states. Thus, it appears that the levels, function, and distribution of the Rad51 protein within cells may be monitored as a diagnostic tool of cellular health or fate. In addition, due to Rad51's essential role in a number of cellular processes, Rad51 is an important target molecule to screen candidate drug agents which can modulate its biological activity.

Accordingly, in a preferred embodiment, the invention provides methods of diagnosing individuals at risk for a disease state. As will be appreciated by those in the art, "at risk for a disease state" means either that an individual has the disease, or is at risk to develop the disease in the future. By "disease state" herein is meant a disease that is either caused by or results in aberrant Rad51 distribution or biological activity. For example, as is more fully described below, aberrant distribution of Rad51 foci in a cell can be indicative of cancer, apoptosis, cellular stress, etc., which can lead to the development of disease states. Similarly, disease states caused by or resulting in aberrant Rad51 biological activity, including alterations caused by mutation, changes in the cellular amount or distribution of Rad51, and changes in the biological function of Rad51 , for example altered nucleic acid binding, filament formation, DNA pairing (i.e. D-loop formation), strand-exchange, strand annealing or recombinogenicity, are also included within the definition of disease states which are related to or associated with Rad51.

Thus, disease states which may be evaluated using the methods of the present invention include, but are not limited to, cancer (including solid tumors such as skin, breast, brain, cervical carcinomas, testicular carcinomas, etc.), diseases associated with premature or incorrect apoptosis, including AIDS, cancers (e.g. melanoma, hepatoma, colon cancer, etc.), liver failure, Wilson disease, myelodysplastic syndromes, neurodegenerative diseases, multiple sclerosis, aplastic anemia, chronic neutropenia, Type I diabetes mellitus, Hashimoto thyroiditis, ulcerative colitis, Canale-Smith syndrome, lymphoma, leukemia, solid tumors, and autoimmune diseases), diseases associated with cellular stress which is affiliated with nucleic acid modification, including diseases associated with oxidative stress such as cardiovascular disease, immune system function decline, aging, brain dysfunction and cancer.

In one embodiment, the method comprises first determining the distribution of Rad51 foci in a first tissue type of a first individual, i.e. the sample tissue for which a diagnosis is required. In some embodiments, the testing may be done on single cells. The first individual, or patient, is suspected of being at risk for the disease state, and is generally a human subject, although as will be appreciated by those in the art, the patient may be animal as well, for example in the development or evaluation of animal models of human disease. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

As will be appreciated by those in the art, the tissue type tested will depend on the disease state under consideration. Thus for example, potentially cancerous tissue may be tested, including breast tissue, skin cells, solid tumors, brain tissue, etc. Similarly, cells or tissues of the immune system, including blood, and lymphocytes; cells or tissues of the cardiovascular system (for example, for testing oxidative stress).

In a preferred embodiment, the disease state under consideration is cancer and the tissue sample is a potentially cancerous tissue type. Of particular interest is breast, skin, brain, colon, prostate, and other solid tumor cancers. As outlined in the Examples, cultured breast cancer cells and primary invasive breast cancer cells all demonstrate an increase in the presence of Rad51 foci.

Similarly, several diseases caused by defective nucleotide excision repair (NER) systems, including Xeroderma pigmentosum, show increased Rad51 foci.

In a preferred embodiment, primary cancerous tissue is used, and may show differential Rad51 staining. While the number of cells exhibiting Rad51 foci may be less than for cell lines, primary cancerous tissue shows an increase in Rad51 foci. Thus for example, from 0.05 to 10% of primary cancerous cells exhibit differential Rad51 foci, with from about 1 to about 5% being common.

It should be noted that not all cancer cell lines exhibit aberrant Rad51 protein foci. For example, the ovarian cancer cell line Hey does not show an increase in Rad51 foci. Similarly, as outlined in the examples, transformed but non-malignant human cells can show an increased percentage of Rad51-positive cells (compared to non-transformed cells), although it is generally not as great as in tumor cells.

In a preferred embodiment, the disease state under consideration involves apoptosis, and includes, but is not limited to, including AIDS, cancers (e.g. melanoma, hepatoma, colon cancer, etc.), liver failure, Wilson disease, myeodysplastic syndromes, neurodegenerative diseases, multiple sclerosis, aplastic anemia, chronic neutropenia, Tupe I diabetes mellitus, Hashimoto thyroiditis, ulcerative colitis, Canale-Smith syndrome, lymphoma, leukemia, solid tumors, and autoimmune diseases. This list includes disease states that include too much as well as too little apoptosis. See Peter et al., PNAS USA 94:12736 (1997), hereby incorporated by reference.

In a preferred embodiment, the disease state under consideration involves cellular stress associated with nucleic acid modification, including aging, cardiovascular disease, declines in the function of the immune system, brain dysfunction, and cancer.

The distribution of Rad51 foci is determined in the target cells or tissue. To date, two main types of Rad51 foci have been identified. As reported earlier (Haaf, 1995, supra) in situ immunostaining with Rad51 antibodies reveals three kinds of nuclei: 1) nuclei that did not show any staining at all (no foci); 2) nuclei that showed weak to medium staining and showed only a few foci (Type I nuclei); and 3) nuclei that showed strong staining and showed many foci (Type II nuclei). In general, the staining is excluded from the cytoplasm. Type I and Type II patterns of nuclei staining are shown in FIG. 1; many of the foci have a double-dot appearance, typical of paired DNA segments. In normal cells, type I nuclei are found in 7–10% of cells and type II nuclei in less than 0.4 to 1% of cells, with generally about 90% of the cells showing no foci. In contrast, some cells involved in disease states show a marked increase in Rad51 foci. As outlined herein and shown in the examples, the numbers of cells showing Rad51 foci in cells associated with disease states is significantly increased. Thus, in a preferred embodiment, the number of cells showing type I nuclei is generally from about 5% to about 50% of the nuclei, with from about 10% to about 40% generally being seen. Thus, in a preferred embodiment, there is at least a 5% increase in the type I foci, with at least about 10 % being preferred, and at least about 30% being particularly preferred. Generally, to see this effect, at least about 100 cells should be evaluated, with at least about 500 cells being preferred, and at least about 1000 being particularly preferred.

Similarly, the number of cells showing type II nuclei also increases, with from about 1% to about 10% of the nucleic exhibiting type II foci and from about 1% to about 5% being common. Thus, in a preferred embodiment, there is at least a 5% increase in type II foci, with at least about 10% being preferred, and at least about 30% being particularly preferred. In a preferred embodiment, both types of foci increase simultaneously. In alternate embodiments, only one type of foci increases.

Similarly, an increase in both types of foci (i.e. an increase in any foci, irrespective of type) can also be evaluated using the same numbers.

The distribution of Rad51 foci can be determined in a variety of ways. In a preferred embodiment, a labeled binding agent that binds to Rad51 is used to visualize the foci. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Preferred labels are fluorescent or radioactive labels. The binding agent can either be labeled directly, or indirectly, through the use of a labeled secondary agent which will bind to the first binding agent. The cells or tissue sample is prepared as is known for cellular or in situ staining, using techniques well known in the art, as outlined in the Examples.

In a preferred embodiment, the binding agent used to detect Rad51 foci is an antibody. The antibodies may be either polyclonal or monoclonal, with monoclonal antibodies being preferred. In general, it is preferred, but not required, that antibodies to the particular Rad51 under evaluation be used; that is, antibodies directed against human Rad51 are used in the evaluation of human patients. However, as the homology between different mammalian Rad51 molecules is quite high (73% identity as between human and chicken, for example), it is possible to use antibodies against Rad51 from one type of animal to evaluate a different animal (mouse antibodies to evaluate human tissue, etc.). Thus, in a preferred embodiment, antibodies raised against eukaryotic Rad51 are used, with antibodies raised against mammalian Rad51 being especially preferred. Thus, antibodies raised against yeast, human, rodent, primate, and avian Rad51 proteins are particularly preferred. In addition, as will be appreciated by those in the art, the protein used to generate the antibodies need not be the full-length protein; fragments and derivatives may be used, as long as there is sufficient immunoreactivity against the sample Rad51 to allow detection. Alternatively, other binding agents which will bind to Rad51 at sufficient affinity to allow visualization can be used.

Without being bound by theory, as outlined in the Examples, it does not appear that the quantitative amount of Rad51 protein is necessarily altered in cells exhibiting the presence or altered distribution of foci. However, in some circumstances the quantitative amount of Rad51 may be measured and correlated to the presence or absence of Rad51 foci.

In addition, the appearance of the foci may be used in the determination of the presence of aberrant Rad51 foci. As noted in the Examples, in some cases linear "strings" of 5–10 Rad51 foci are formed, with somatic association of "homologous" strings of similar length, tightly paired at one of the ends. These structures are generally associated with DNA fibers, as is shown in the Figures. Thus, the formation of these types of structures can be indicative of aberrant Rad51 foci.

Furthermore, in a preferred embodiment, particularly in disease states involving apoptosis and DNA damage, aberrant Rad51 foci includes the development of micronuclei containing Rad51. As shown in the Examples, evaluation of Rad51 foci over time, in particular after cellular stress, can lead to the concentration and exclusion of the Rad51 foci (which are associated with DNA) into micronuclei, which frequently is accompanied by genome fragmentation. This effect is seen in a wide variety of apoptotic cells, as is shown in the Examples, even in the absence of induced DNA damage, such as through the use of colcemid, a spindle poison, thus indicating the role of Rad51 in normal apoptotic pathways. In addition to the evaluation of the presence or absence of Rad51 foci, the cells may be evaluated for cell cycle arrest, as is outlined in the Examples.

Once the distribution of Rad51 foci has been determined for the target sample, the distribution of foci is compared to the distribution of Rad51 foci from a second cell or tissue type. As will be appreciated by those in the art, the second tissue sample can be from a normal cell or tissue from the original patient or a tissue from another, unaffected individual, which has been matched for correlation purposes. A difference in the distribution of Rad51 foci as between the first tissue sample and the second matched sample indicates that the first individual is at risk for a disease state which results in aberrant Rad51 loci.

In a prefer-red embodiment, the difference in Rad51 foci distribution is an increase in Rad51 foci, of either type 1 or type 2 foci, as outlined above. In an alternate embodiment, the difference in Rad51 foci distribution is a decrease in the number of Rad51 foci.

In some embodiments, there need not be a direct comparison. For example, having, once shown that a particular normal tissue only contains a small percentage of Rad51 foci, the tissue or cells under evaluation may not need to be compared to a control sample; the presence of a hi-,her percentage allows the diagnosis. Thus, for example, in breast cancer, the presence of at least 1% of the cells containing Rad51 foci is indicative that the patient is at risk for breast cancer or in fact already has it.

In a preferred embodiment, a difference in the distribution of Rad51 foci, in particular an increase in Rad51 foci, indicates that the cell or tissue is cancerous.

In a preferred embodiment, a difference in the distribution of Rad51 foci, in particular an increase in Rad51 foci, indicates that the cell or tissue is apoptotic. These differences can include the association of Rad51 with DNA fibers, the association of Rad51 with damaged DNA in micronuclei, or the presence of Rad51 in micronuclei.

In addition, in a preferred embodiment, the extent of aberrant distribution indicates the severity of the disease state. Thus, for example, high percentages of cells containing Rad51 foci can be indicative of highly malignant cancer.

In addition to the evaluation of Rad51 foci, the presence or absence of variant (mutant) Rad51 genes may also be used in diagnosis of disease states. Mutant forms of p53 have been found in roughly 50% of known cancers, and it is known that Rad51 and p53 can interact on a protein level. In addition, p53 and Rad51 have somewhat similar biochemical functions. Thus, the present discovery that Rad51 plays a pivotal role in some cancers and apoptosis thus suggests that variant Rad51, or incorrectly controlled Rad51 levels or functions may be important in some disease states.

Accordingly, in a preferred embodiment, the present invention provides methods for identifying a cell containing a mutant Rad51 gene comprising determining the sequence of all or part of at least one of the endogenous Rad51 genes. By "variant Rad51 gene" herein is meant any number of mutations which could result in aberrant Rad51 function or levels. Thus, for example, mutations which alter the biochemical function of the Rad51 protein, alter its half-life and thus its steady-state cellular level, or alter its regulatory sequences to cause an alteration in it's steady-state cellular level may all be detected. This is generally done using techniques well known in the art, including, but not limited to, standard sequencing techniques including sequencing by PCR, sequencing-by-hybridization, etc.

Similarly, in a preferred embodiment, the present invention provides methods of identifying the Rad51 genotype of an individual or patient comprising determining all or part of the sequence of at least one Rad51 gene of the individual. This is generally done in at least one tissue of the individual, and may include the evaluation of a number of tissues or different samples of the same tissue. For example, putatively cancerous tissue of an individual is the preferred sample.

The sequence of all or part of the Rad51 gene can then be compared to the sequence of a known Rad51 gene to determine if any differences exist. This can be done using any number of known homology programs, such as Bestfit, etc.

In a preferred embodiment, the presence of a difference in the sequence between the Rad51 gene of the patient and the known Rad51 gene is indicative of a disease state or a propensity for a disease state.

The present discovery relating to the role of Rad51 in cancer and apoptosis thus provide methods for inducing apoptosis in cells. In a preferred embodiment, the methods comprise increasing the activity of Rad51 in the cells. By "biological activity" of Rad51 herein is meant one of the biological activities of Rad51, including, but not limited to, the known Rad51 DNA dependent ATPase activity, the nucleic acid strand exchange activity, the formation of foci, single-stranded and double-stranded binding activities, filament formation (similar to the recA filament of yeast), pairing activity (D-loop formation), etc. See Gupta et al., supra, and Bauman et al., supra, both of which are expressly incorporated by reference herein. As will be appreciated by those in the art, this may be accomplished in any number of ways. In a preferred embodiment, the activity of Rad51 is increased by increasing the amount of Rad51 in the cell, for example by overexpressing the endogenous Rad51 or by administering a gene encoding Rad51, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety.

In a preferred embodiment, the cells which are to have apoptosis induced are cancer cells, including, but not limited to, breast, skin, brain, colon, prostate, testicular, ovarian, etc. cancer cells, and other solid tumor cells.

In a preferred embodiment, the methods may also comprise subjecting the cells to conditions which induce nucleic acid damage, as this appears to provide a synergistic effect, as outlined above.

In a preferred embodiment, the methods further comprise increasing the activity of p53 in the cell, for example by increasing the amount of p53, as outlined above for Rad51.

The present discoveries relating to the pivotal role of Rad51 in a number of important cellular processes and disease states also makes Rad51 an important target in drug screening. Thus, in a preferred embodiment, the present invention provides methods for screening for a bioactive agent which may bind to Rad51 and modulate its activity.

In a preferred embodiment, the methods are used to screen candidate bioactive agents for the ability to bind to Rad51. In this embodiment, the methods comprise adding a candidate bioactive agent to a sample of Rad51 and determining the binding of the candidate agent to the Rad51. By "candidate bioactive agent" or "candidate drugs" or grammatical equivalents herein is meant any molecule, e.g. proteins (which herein includes proteins, polypeptides, and peptides), small organic or inorganic molecules, polysaccharides, polynucleotides, etc., which are to be tested for the capacity to bind and/or modulate the activity of Rad51. Candidate agents encompass numerous chemical classes. In a preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. Any number of techniques are available for the random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications to produce structural analogs.

In a preferred embodiment, candidate bioactive agents include proteins, nucleic acids, and organic moieties.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening against Rad51. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Patent No. 5,644,048), phosphorodithioate (Briu et al., J. Am. Chem. Soc. 111:2321 (1989), methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

The candidate agents are added to a sample of Rad51 protein. As is outlined above, all or part of a full-length Rad51 protein can be used, or derivatives thereof. Generally, the addition is done under conditions which will allow the binding of candidate agents to the Rad51 protein, with physiological conditions being preferred.

The binding of the candidate agent to the Rad51 sample is determined. As will be appreciated by those in the art, this may be done using any number of techniques.

In one embodiment, the candidate bioactive agent is labelled, and binding determined directly.

Where the screening assay is a binding assay, one or more of the molecules may be joined to a label, where the label can directly or indirectly provide a detectable signal. Various labels include radioisotopes, fluorescent molecules, enzyme reporters, colorimetric reporters, chemiluminescers, specific binding molecules, particles, e.g. magnetic or gold particles, and the like. Specific binding molecules include pairs, such as biotin and streptavidin, digoxygenin and antidigoxygenin etc. For the specific binding members, the complementary member would normally be labeled with a molecule which provides for detection, in accordance with known procedures.

In some embodiments, only one of the components is labeled. For example, the Rad51 may be labeled at tyrosine positions using $^{125}$I. Alternatively, more than one component may be labeled with different labels; using $^{125}$I for the Rad51, for example, and a fluorophor for the candidate agents.

In a preferred embodiment, the binding of the candidate bioactive agent is determined directly. For example, the Rad51 may be attached to a solid support such as a microtiter plate or other solid support surfaces, and labelled candidate agents added under conditions which favor binding of candidate agents to the Rad51 protein. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagents are washed off, the system is evaluated for the presence of the label, which is indicative of an agent which will bind to the Rad51. The agent which binds can then be characterized or identified as needed.

In a preferred embodiment, the binding of the candidate bioactive agent is determined through the use of competitive binding assays. In this embodiment, the competitor is can be any molecule known to bind to Rad51, for example an antibody to Rad51, or one of the proteins known to interact with Rad51, including Rad52, Rad54, Rad55, DMC 1, BRCA1, BRCA2, p53, UBC9, RNA polymerase II, and Rad51 itself, any or all of which may be used in competitive assays. Either the candidate agents or the competitor may be labeled, or both may be labeled with different labels. In this embodiment, either the candidate bioactive agent, or the competitor, is added first to the Rad51 sample for a time sufficient to allow binding, if present, as outlined above. Excess reagent is generally removed or washed away. The second component is then added, and the presence or absence of the labeled component is followed, to indicate binding.

In a preferred embodiment, methods for screening for a bioactive agent capable of modulating the activity of Rad51 comprise the steps of adding a candidate bioactive agent to a sample of Rad51, as above, and determining an alteration in the biological activity of Rad51. "Modulating the activity of Rad51" includes an increase in activity, a decrease in activity, or a change in the type or kind of activity present. Thus, in this embodiment, the candidate agent should both bind to Rad51 (although this may not be necessary), and alter its biological or biochemical activity as defined above.

Thus, in this embodiment, the methods comprise combining a Rad51 sample and a candidate bioactive agent, and testing the Rad51 biological activity as is known in the art to evaluate the effect of the agent on the activity of Rad51.

In a preferred embodiment, the methods include both in vitro screening methods, as are generally outlined above, and in vivo screening of cells for alterations in the presence, distribution or activity of Rad51. Accordingly, in a preferred embodiment, the methods comprise the steps of adding a candidate bioactive agent to a cell, and determining the effect on the formation or distribution of Rad51 foci in the cell. The addition of the candidate agent to a cell will be done as is known in the art, and may include the use of nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val), Kalderon (1984), et al., Cell, 39:499–509; the human retinoic acid receptor-β nuclear localization signal (ARRRRP); NFκB p50(EEVQRKRQKL; Ghosh et al., Cell 62:1019 (1990); NFκB p65 (EEKRKRTYE; Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990. In general, the Rad51 foci will be evaluated as is generally discussed above.

In a preferred embodiment, the methods comprise adding a candidate bioactive agent to a cell, and determining the effect on double strand break repair, homologous recombination, sensitivity to ionizing radiation, and class switch recombination. Assays are detailed in Park, J. Biol. Chem. 270(26):15467 (1995) and Li et al., PNAS USA 93:10222 (1996), Shinohara et al., supra, 1992, all of which are hereby incorporated by reference.

In a preferred embodiment, the cells to which candidate agents are added are subjected to conditions which induce nucleic acid damage, including the addition of radioisotopes ($I^{125}$, Tc, etc., including ionizing radiation and uv), chemicals (Fe-EDTA, bis(1.10-phenanthroline), etc.), enzymes (nucleases, etc.).

A variety of other reagents may be included in the screening assays or kits, below. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, antimicrobial agents, etc., may be used. In general, the mixture of components may be added in any order that provides for the requisite binding.

Once identified, the compounds having the desired pharmacological activity may be administered in a physiologically acceptable carrier to a host, as previously described. The inhibitory agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, aerosols, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

In a preferred embodiment, kits are provided. The kits can be utilized in a variety of applications, including determining the distribution of Rad51 foci, diagnosing an individual at risk for a disease state, including cancer, diseases associated with apoptosis, and diseases associated with stress (including oxidative stress, hypoxic stress, osmotic stress or shock, heat or cold stress or shock). The kits include a Rad51 binding agent, that will bind to the Rad51 with sufficient affinity for assay. Antibodies are preferred binding agents. The kits further include a detectable label such as is outlined above. In one embodiment, the Rad51 binding agent is labeled; in an additional embodiment, a secondary binding agent or label is used. Thus for example, the binding agent may include biotin, and the secondary agent can include streptavidin and a fluorescent label. Additional reagents such as outlined above can also be included. Furthermore, the kit may include packaging and instructions, as required.

The identification of the crucial role of Rad51 in a number of cellular processes and disease states also identifies a number of methods and compositions relating to combinations of Rad51 and other tumor suppressor genes. Thus, Rad51 may function interactively with a number of tumor suppressor genes and thus compositions comprising combinations of these genes may be useful in methods of gene therapy treatment and diagnosis.

Accordingly, in a preferred embodiment, compositions comprising a nucleic acid encoding a Rad51 protein and at least one nucleic acid encoding a tumor suppressor gene are provided. Suitable tumor suppressor genes include, but are not limited to, p53, and the BRCA genes, including BRCA1 and BRCA2 genes. Thus, preferred embodiments include compositions of nucleic acids encoding a) a Rad51 gene and a p53 gene; b) a Rad51 gene and a BRCA1 gene; c) a Rad51 gene and a BRCA2 gene; d) a Rad51 gene, a p53 gene, and a BRCA gene; and e), a Rad51 gene, a p53 gene, a BRCA1 gene and a BRCA2 gene.

In an additional embodiment, the compositions comprise recombinant proteins. By "recombinant" herein is meant a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In a preferred embodiment, these compositions can be administered to a cell or patient, as is outlined above and generally known in the art for gene therapy applications.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are specifically incorporated by reference.

EXAMPLES

Example 1

Immunofluorescent Staining of Human Breast Cancer Cells

Breast tumour cells have mutated p53 and have various types of chromosomal aberrations like insertions, deletions, rearrangements, amplifications etc. Recombination proteins such as Rad51 could evidently participate in such processes. In order to better understand the role of uncontrolled recombination and its role in tumour formation and progression, the status of Rad51 protein in breast tumour cells by staining them with anti Rad51 antibodies was done.

Detailed methods of cloning and expression of HsRad51 gene in *E. coli*, purification of recombinant HsRad51 protein with six histidine residues at it's aminoterminal end and preparation of ployclonal antibodies against HsRad51 protein were described previously by Haaf, Golub et al. 1995, supra, which is expressly incorporated herein by reference.

Immunofluorescent staining with anti-Rad51 protein antibodies. Monolayer cultures of different cell substrates (see table 1) were grown in Dulbecco's MEM medium supplemented with 10% fetal bovine serum and antibiotics. The cells were detached from culture flasks by gentle trypsinization, pelleted and resuspended in phosphate buffered saline (PBS; 136 mM NaCl, 2 mM KCl, 10.6 mM $Na_2HPO_4$, 1.5 mM $KH_2PO_4$ [pH 7.3]) prewarmed at 37° C. For immunofluorescence staining standard protocols were used (Haaf 1995, supra). Cultured cells were washed and resuspended in PBS. The density of somatic cells was adjusted to about $10^5$ cells per ml in PBS. Aliquots (0.5 ml) of the cell suspension were centrifuged onto clean glass slides at 800 rpm for 4 min, in a Cytospin (Shandon, Pittsburg). Immediately after cytocentrifugation, the slides were fixed in −20° C. methanol for 30 min and then immersed in ice-cold acetone for a few seconds to permealize the cells for antibody staining. Following three washes with PBS, the preparations were incubated at 37° C. with rabbit anti-HsRad51 antiserum, diluted 1:50 with PBS containing 0.5% bovine serum albumin, in a humidified incubator for 30 min. The slides were washed three times for 10 min each and then incubated for 30 min with fluorescein-isothiocyanate (FITC)- conjugated anti-rabbit IgG diluted 1:20 with PBS. After three washes with PBS, the preparations were counterstained with 4',6-diamidino-2-phenylindole (DAPI; 0.1 ug/ml for 1 min) and mounted in antifade {90% (vol/vol) glycerol/0.1 m tris-HCl pH 8.0)/ 2.3% 1,4-diazabicyclo[2.2.2]octane (DABCO)}.

Digital Imaging Microscopy. Images were taken with a Zeiss epifluorescence microscope with a thermo-electronically cooled charge coupled device (CCD) camera (model PM512; Photometrics, Tucson, Ariz.) which was controlled by an Apple Macintosh computer. Grey scale source images were captured separately with filter sets for fluorescein and DAPI. Gray scale source images were pseudocolored and merged using ONCOR Image and ADOBE Photoshop software. It is worth emphasizing that although a CCD imaging system was used, all antibody signals were clearly visible by eye through the microscope.

To study the possible involvement of Rad51 in tumorigenesis we compared the in situ localization of Rad51 protein homologs in different cell substrates i.e. mortal fibroblast strains, virus-transformed non-malignant cell lines and tumor cell lines (see table). A specific rabbit antiserum raised against human Rad51 protein was used in these studies. These antibodies reacted mainly with Rad51 protein in mammalian cell extracts as judged by Western blotting (see FIG. No 2 in (Haaf, Golub et al. 1995). Immunostaining of different cells showed that HsRad51 is concentrated in small and discrete sites (foci) through out nucleoplasm and is largely excluded from nucleoli and cytoplasm. At least 250 nuclei of exponentially growing cultures were analyzed for each experiment. As reported earlier (Haaf, Golub et al. 1995) immunostaining revealed three kinds of nuclei: 1) nuclei that did not show any staining at all (no foci), 2) nuclei that showed weak to medium staining and showed only a few foci (Type I nuclei) 3) nuclei that showed strong staining and showed many foci (Type II nuclei). In normal fibroblast control cells, we found type I nuclei in about 10% of cells and type II nuclei in less than 0.4 to 1% of cells and about 90% of the cells showed no foci. Use of preimmune serum, as well as omission of either the primary or secondary antibody, resulted in the absence of focally concentrated nuclear immunofluorescence.

As reported earlier (Haaf, Golub et al. 1995) in normal (mortal) fibroblast control cells (Hs68) we found type I nuclei in 7%–10% of cells and type II nuclei in less than 0.4% of cells, where as 90% or more of the cells showed no foci (Table 1). In contrast all breast tumor cell lines tested (BT20, SrBr3, MoF7) exhibited 1–5% of type II nuclei and 10–38% of type I nuclei (Table 1). Transformed but non-malignant human cells, i.e. SV 40 transformed fibroblasts (LNL8, 63L7), EBV-transformed lymphoblasts (GM 01194), and adenovirus-transformed kidney cells (293) also showed an increased percentage of Rad51-positive cells (compared to normal fibroblasts), however the numbers observed were lower than in tumor cells. Interestingly, some tumor substrates i.e. the ovarian cancer line Hey; did not show a significant increase of Rad51-positive cells.

As demonstrated earlier (Haaf, Golub et al. 1995), when the normal fibroblast cells were exposed to DNA damaging agents like 137Cs, there was a significant increase of cells containing type I and type II nuclei (Table 2). It is worth emphasizing that non-irradiated breast tumor cells show approximately the same percentage of Rad51-positive nuclei as Hs68 fibroblasts exposed to 900 rad Cs137 which kills 99% of cells (Table 2). The immunofluorescent patterns of (non-irradiated) breast cancer cells (FIG. 1) and fibroblasts that were exposed to DNA damaging agents are identical.

When the breast cancer cells were exposed to Cs137, the increase in the number of cells with type I and type II nuclei was even more dramatic than in normal (Hs68) or transformed (LNL8) fibroblasts (Table 2). Up to 40% of irradiated breast cancer cells showed type I nuclei and 11%–18% showed type II nuclei.

In order to rule out any artifacts that would arise due to the examination of cultured breast cancer cells, we then examined the breast tissue obtained directly from the patient for Rad51 positive staining. Immunohistochemical evaluation revealed definite nuclear staining of invasive breast carcinoma cells. Specifically, nuclear reactivity could be demonstrated in sections obtained from three paraffin-embedded samples. The nuclear staining appeared granular in some areas, and in others, occupied the entire nucleus. The actual number of invasive carcinoma cells that fluoresced was quite small, and estimated to be less than 5% of the nuclei seen in three samples with definite reactivity FIG. 2). Nuclear staining was not identical in normal breast epithelium or lactating breast tissue. Bright nuclear reactivity was seen in positive control testicular tissue, specifically, in the cells lining the seminiferous tubules. Background staining did not appear to be problematic.

Increase in immunofluorescence of HsRad51 in breast cancer cells can result from either increase in the amount of Hsrad51 in these cells or it could be seen as a result of re-organization of Hsrad51 in these nuclei in response to damage related activities. We think that the latter is true because there was no apparent increase in the amount HsRad51 in breast cancer cells as shown by the Western blots (data not shown).

The molecular basis and the consequence of the increase in HsRad51 in breast cancer cells is not clear. Since Rad51 protein interacts with other proteins of the Rad52 epistasis group and these multiprotein complexes are involved in the recombinational repair of double-strand breaks (Hays, et al., (1995). Proc. Natl. Acad. Sci. USA 92: 6925–6929; Johnson, R. D. and L. S. Symington (1995). Mol. Cell. Biol. 15: 4843–4850), it is tempting to speculate that these foci are the sites where repair/recombination events are taking place. Since p53 is known to interact with Rad51 it will be interesting to see the colocalization of p53 and Rad51 protein in these complexes. It is quite possible that these foci contain either wild type or mutant p53 and other breast cancer related proteins like BRCA1, BRCA2 or the newly discovered STG1 protein. We propose that the increase in the immunofluorescence of Rad51 in the breast cells can be used as an important cytological marker for cell proliferation and malignant cell growth. Further experimentation will be done to validate this proposal and to understand the role of increase in Rad51 foci and carcinogenesis.

TABLE 1

Percentage of nuclei containing discrete foci enriched with HsRad51 protein.

| Cell Substrate | | No foci | Type I | Type II |
|---|---|---|---|---|
| Hs68 | Normal fibroblasts | 90% | 10% | 0% |
| | | 93% | 7% | 0% |
| LNL8 | Transformed fibroblasts | 90% | 9% | 1% |
| (NI 00847) | (SV 40) | 90% | 8% | 2% |
| 63L7 | Transformed fibroblasts | 94% | 6% | 0% |
| | (SV40) | 94% | 3% | 3% |
| GM01194 | Transformed lymphoblasts | 91% | 7% | 2% |
| | (EBV) | 90% | 9% | 1% |
| | | 92% | 8% | 0% |
| | | 80% | 18% | 2% |
| | | 80% | 19% | 1% |
| 293 Cells | Transformed kidney cells | 75% | 23% | 2% |
| | (Adenovirus) | 83% | 15% | 2% |
| | | 82% | 17% | 1% |
| BT20 | Breast cancer line | 86% | 10% | 4% |
| | | 82% | 13% | 5% |
| | | 78% | 17% | 5% |
| SrBr3 | Breast cancer line | 74% | 25% | 1% |
| MoF7 | Breast cancer line | 57% | 38% | 5% |
| | | 88% | 10% | 2% |
| Tera2 | Testicular teratoma | 76% | 23% | 1% |
| | | 77% | 22% | 1% |
| Hey | Ovarian cancer line | 94% | 5% | 1% |
| | | 98% | 2% | 0% |
| HeLa | Cervix (?) tumor cells | 67% | 31% | 2% |

TABLE 2

Percentage of nuclei containing discrete foci enriched with HsRad51 protein.

| Cell substrate | Treatment | No foci | Type I | Type II |
|---|---|---|---|---|
| Hs68 | None | 90% | 10% | 0% |
| (normal | None | 93% | 7% | 0% |
| fibroblasts) | 6 hrs after 10 rad Cs137 | 96% | 4% | 0% |
| | 6 hrs after 50 rad Cs137 | 96% | 4% | 0% |
| | 6 hrs after 150 rad Cs137 | 92% | 7% | 1% |
| | 6 hrs after 450 rad Cs137 | 88% | 8% | 4% |
| | 6 hrs after 900 rad Cs137 | 91% | 4% | 5% |
| LNL8 | None | 90% | 9% | 1% |
| (NI 00847) | | | | |
| (SV40- | None | 90% | 8% | 2% |
| transformed | | | | |
| fibroblasts) | 6 hrs after 150 rad Cs137 | 88% | 11% | 1% |
| | 6 hrs after 300 rad Cs137 | 76% | 19% | 5% |
| | 6 hrs after 900 rad Cs137 | 78% | 17% | 5% |
| BT20 | None | 86% | 10% | 4% |
| (breast cancer | None | 82% | 13% | 5% |
| cells) | None | 78% | 17% | 5% |
| | 6 hrs after 300 rad Cs137 | 44% | 41% | 11% |
| | 6 hrs after 900 rad Cs137 | 52% | 30% | 18% |

Example 2

Nuclear Foci of Human Recombination Protein Rad51 in Nucleotide Excision Repair Defective Cells Eukaryotic cells have several different mechanisms for repairing damaged DNA (for review see R. Wood, 1996). One of the major pathway is nucleotide excision repair (NER), which excises damage within oligomers that are 25–32 nucleotides long. Patients with recessive heredity disorder XP have defects in one of several enzymes, which participate in ER. There are seven XP groups (XP-A to XP-G), which have defects in the initial steps of the DNA excision repair.

DNA damage is removed several-fold faster from transcribed genes than from non-transcribed, mainly due to preferential NER of the transcribed strand (for review see Hanawalt, 1994). This mechanism does not function in Cockayne's syndrome (CS) patients.

NER defective cells, evidently, sustain increased amount of DNA damage. Thus we evaluated NER defective cells from XP and CS cells for an increased amount of Rad51 protein foci.

To study possible effect of NER on localization of HsRad51 in somatic tissue culture cells, we compare in situ localization of the protein in normal fibroblasts, different XP cells and CS-B cells. A policlonal rabbit antiserum raised against human Rad51 protein was used in this study. These antibody reacted in mammalian cell extract mainly with Rad51 protein as judged by Western Blotting (see FIG. 2 in Haaf et al., 1995). Immunostaining of different cell lines showed that HsRad51 is concentrated in small and discrete sites (foci) throughout nucleoplasm and is largely excluded from nucleoli and cytoplasm. As discussed above, immunostaining revealed three kinds of nuclei, types I, II and III. The results are shown in Table 3.

TABLE 3

Percentage of nuclei containing discrete foci enriched with HsRad51 protein

| Cell substrate | | No foci | Type I* | Type II* |
|---|---|---|---|---|
| Hs68 | Normal fibroblasts | 90% | 10% | 0% |
| 63L7 | Normal fibroblasts | 94% | 6% | 0% |
| 63L7 (confluent) | FA fibroblasts | 94% | 3% | 3% |
| 6935 | FA fibroblasts | 92% | 6% | 2% |
| 6914 | Normal | 72% | 21% | 7% |
| 6914 | lymphoblasts | 72% | 25% | 3% |
| 6914 | | 67% | 24% | 9% |
| GM01194 | Normal | 91% | 7% | 2% |
| GM01194 | lymphoblasts | 90% | 9% | 1% |
| GM01194 | | 92% | 8% | 0% |
| GM07063 | FA lymphoblasts | 90% | 8% | 2% |
| GM07063 | FA lymphoblasts | 96% | 4% | 0% |
| GM13020 | FA lymphoblasts | 92% | 7% | 1% |
| GM13022 | | 86% | 13% | 1% |
| GM13022 | | 78% | 20% | 2% |
| GM13023 | | 94% | 5% | 1% |
| GM13071 | | 81% | 15% | 4% |
| GM13071 | | 74% | 23% | 3% |

*Type I nuclei show only few (<15) foci and/or weak to medium HsRad51 immunofluorescence, whereas Type II cells show many and/or strongly fluorescing foci.
250 nuclei were analyzed for each experiment.

In normal (mortal) fibroblast control cells, LNL8 and NF, we found type I nuclei in 5–9% cells and type II nuclei in 1–7% cells, where as 88–90% of the cells showed no foci (Table 3). Use of preimmune serum, as well as omission of either the primary or secondary antibody, resulted in the absence of focally concentrated nuclear immunofluorescence.

XP-V cells are normal in NER, but have defect in postreplication repair process (Boyer et al., 1990; Griffiths et al., 1991; Wang et al., 1991, 1993). As we expected, these cells showed the same distribution pattern of nuclear HsRad51 as control cell lines (Table 3).

Distribution of HsRad51 foci in CS-B cells also was similar to the cells with normal NER (Table 3). This result was also anticipated. CS-B cells are defective in NER which is coupled with transcription (Venema et al., 1990). Transcribed genes, evidently, comprise only a small part of the whole genomic DNA and damage in transcribed genes, therefore, should be accounted for only a very small fraction of the damage in genomic DNA.

XP-A, XP-B, XP-F and XP-G cells are all defective in NER. XP-A cells have defect in XPA protein, which carries out a crucial rate-limiting step in NER-recognition of DNA lesion (Jones and Wood, 1993). The protein makes a ternary complex with ERCC1 protein and XPF protein, which is defective in XP-F cells (Park and Sankar, 1994). XP-B and XP-G cells are defective in different steps of NER which follow damage recognition (Reviewed in Ma et al., 1995).

XP-A and XP-F cell lines have increased amount of cells with HsRad51 protein foci (Table 3). In contrast, XP-B and XP-G cells have about the same level of HsRad51 protein foci, as cells with normal NER (Table 3). This result could be easily understood if we assume, that 1) formation of HsRad51 foci is caused by DNA damage, b) DNA lesion is excluded from the pool of damage DNA which cause Rad51 foci formation as soon as XPA/XPF/ERCC1 complex binds to the lesion. DNA damage in XP-B and XP-G cells is recognized by NER system, but the damage cannot be proceeded and removed by the system. Such unremoved damage, evidently, is not considered as a substrate for Rad51 protein involved repair as soon as the damage is recognized by NER complex XPA/XPF/ERCC 1 as a substrate for NER, even if defect in subsequent steps of NER makes its removing impossible.

Induction of principal DNA repair system (SOS respond) in *E. coli* is, assumed to be triggered by formation of single-stranded DNA (ssDNA) which results from DNA damage (reviewed in Little and Mount, 1982). DNA damage in XP-A cells is not recognized by NER and, therefore, at least a considerable part of DNA damage is not proceeded to formation of ssDNA regions. Nevertheless, Rad51 foci are effectively formed in XP-A cells and their amount could be further increased by UV or -irradiation (Tables 4 and 5). Evidently, ssDNA is not a primary signal for HsRad51 protein foci formation.

TABLE 4

Percentage of nuclei containing discrete foci enriched with HsRad51 protein

| Cell substrate | Treatment | No foci | Type I* | Type II* |
|---|---|---|---|---|
| LNL8 (control) | No treatment | 90% | 9% | 1% |
| | " | 90% | 8% | 2% |
| NF (control) | No treatment | 88% | 5% | 7% |
| | No treatment | 89% | 5% | 6% |
| XPA | " | | | |
| | " | 51% | 39% | 10% |
| | No treatment | 72% | 20% | 8% |
| | " | 55% | 34% | 7% |
| XPB | | | | |
| | No treatment | 86% | 11% | 3% |
| | " | 86% | 11% | 3% |
| XPD | No treatment | | | |
| | " | 87% | 8% | 5% |
| | No treatment | 63% | 28% | 9% |
| XPF | " | | | |
| | | 48% | 41% | 11% |
| | No treatment | | | |
| | " | 64% | 25% | 8% |
| XPG | | | | |
| | None | 88% | 7% | 5% |
| | | 85% | 9% | 6% |
| XPV | | | | |
| | | 94% | 5% | 1% |
| | | 89% | 11% | 0% |
| CBS | | | | |
| | | 87% | 8% | 5% |

*Type I nuclei show only a few (<15) foci and/or weak to medium HsRad51 immunofluorescence, whereas type II cells show many and/or strongly fluorescing foci.
250 nuclei were analyzed for each experiment.

TABLE 5

Percentage of nuclei containing discrete foci enriched with HsRad51 protein

| Cell substrate | Treatment | No foci | Type I* | Type II* |
|---|---|---|---|---|
| LNL8 (control) | No treatment | 90% | 9% | 1% |
| | No treatment | 90% | 8% | 2% |
| | 6 hrs after 150 rad Cs137 | 88% | 11% | 1% |
| | 6 hrs after 300 rad Cs137 | 76% | 19% | 5% |
| | 6 hrs after 900 rad Cs137 | | | |
| | None | 78% | 17% | 5% |
| | 3 hrs after 300 rad $^{137}$Cs | | | |

TABLE 5-continued

Percentage of nuclei containing discrete foci enriched with HsRad51 protein

| Cell substrate | Treatment | No foci | Type I* | Type II* |
|---|---|---|---|---|
| XPA** |  | 51% | 39% | 10% |
|  | None | 61% | 24% | 15% |
|  | 6 hrs after 900 rad $^{137}$Cs |  |  |  |
|  | None | 72% | 20% | 8% |
|  | 5 hrs after 5 J/m$^2$ UV | 59% | 25% | 16% |
|  | 5 hrs after 15 J/m$^2$ UV | 59% | 34% | 7% |
|  | None | 53% | 31% | 16% |
|  | 5 hrs after 800 rad $^{137}$Cs |  |  |  |
|  | 27 hrs after 800 rad $^{137}$Cs | 55% | 26% | 19% |
| CBS** |  | 87% | 8% | 5% |
|  |  | 60% | 21% | 19% |
|  |  | 77% | 6% | 17% |

*Type I nuclei show only a few (<15) foci and/or weak to medium HsRad51 immunofluorescence, whereas Type II cells show many and/or strongly fluorescing foci.
150 nuclei were analyzed for each experiment.
**Induction of HsRad51 foci in Xeroderma pigmentosum (Type A) implies that single stranded DNA molecules are not the primary signal.
***Induction of HsRad51 foci in cells from patients with Cockayne's syndrome implies that the induction is not dependent on transcription.

In conclusion, human recombination protein HsRad51 is concentrated in multiple discrete foci in nucleoplasm of cultured human cells. After treatment of cells with DNA damaging agents, the percentage of cells with HsRad51 protein immunofluorescence increases. Xeroderma pigmentosum (XP) cells XP-A with inactive protein XPA, responsible for lesion recognition by nucleotide excision repair (NER) system have increased percentage of cells with HsRad51 protein foci. XP-F cells, defective in XPF protein, which forms complex with XPA protein, also have increased level of the HsRad51 protein foci. In contrast, XP-B and XP-G cells with defects in different steps ER, which follow the damage recognition, as well as XP-V cells (normal level of NER) and Cockayne's syndrome (CS) cells (defect in NER, responsible for preferential repair of the transcribed DNA strand) have normal level of HsRad51 protein foci. Evidently, formation of HsRad51 protein foci is caused by DNA damages. DNA damages, however, do not participate in causing formation of HsRad51 protein foci, as soon as they are recognized by NER system, even if the system is blocked on one of the step, leading to DNA repair.

Example 3

Higher Order Nuclear Structures of Rad51 and its Exclusion into Micronuclei After Cell Damage Previous studies have revealed a time- and dose-dependent increase of nuclear HsRad51 protein foci after DNA damage introduced into the genome by various agents (Haaf et al., 1995, supra). Here we show that when the damaged cells are allowed to recover, these Rad51 foci form specific higher-order nuclear structures. Finally, all the focally concentrated Rad51 protein is eliminated into micronuclei that undergo apoptotic genome fragmentation. Treatment of cells with clastogens and aneuploidogens implements a mechanism that affects the nuclear distribution of Rad51 protein and targets Rad51 foci, most likely along with irreversibly damaged DNA into micronuclei. To examine the role of Rad51 protein in DNA repair and cell proliferation, we have analyzed the intranuclear distribution of overexpressed Rad51 protein during the cell cycle and in cell populations proceeding through apoptosis.

Experimental Procedures

Cell Culture. The sources of the cell lines were as follows. Rat TGR-1 cells, J. Sedivy, Brown University; mouse 3T3-Swiss cells, ATCC; human 293 kidney cells, ATCC; human teratoma cells, B. King, Yale University; human LNL8 fibroblasts, S. Meyn, Yale; human XPA and XPF fibroblasts, P Glazer, Yale.

Monolayer cultures were grown in D-MEM medium supplemented with 10% fetal bovine serum and antibiotics. The cells were detached from culture flasks by gentle trypsination, pelleted and resuspended in phosphate-buffered saline (PBS; 136 mM NaCl, 2 mM KCl, 10.6 mM Na$_2$HPO$_4$, 1.5 mM KH$_2$PO$_4$, pH 7.3) prewarmed at 37° C.

To induce DSBs in DNA and recombinational repair, cell cultures were exposed to a $^{137}$CS irradiator at doses of 900 rad and then allowed to recover for various time spans. In another experiment, cells were treated with 10 μM 5-aza-dC for 24 hrs. This hypomethylating base analog is a potent DNA-strand breaker (Snyder, et al., (1989). Mutation Res. 226, 185–190; Haaf, 1995). Incubation of cells with the spindle poison colcemid (1 μg/ml for 24 hrs) resulted in the formation of multinuclei and micronuclei containing entire chromosomes. Under the experimental conditions chosen, colcemid does not cause chromosome breakage. Treatment with etoposide (Sedivy), a drug that inhibits DNA topoisomerase II, is a classic system for inducing apoptosis in cells (Mizumoto, et al., (1994). Mol. Pharmac. 46, 890–895).

Antibody Probes. HsRad51 protein, expressed in E. coli, was isolated and used for preparation of rabbit polyclonal antibodies. Western blotting experiments revealed that rabbit antiserum does not react significantly with any other proteins in mammalian cells except Rad51 (Haaf et al., 1995). Similarly, polyclonal antibodies against HsRad52, a structural homolog of yeast RadS2, were raised in the rat, as is known in the art. Mouse monoclonal antibody 30T14 recognizes Gadd45, a ubiquitously expressed mammalian protein that is induced by DNA damage (Smith, et al., (1994). Science 266, 1376–1380). Monoclonal antibodies H4 and H14 bind specifically to the large subunit of RNAPII (Bregman et al., (1995) J. Cell Biol. 129, 287–298). Monoclonal antibody Pab246 against amino acids 88–93 of mouse p53 was purchased from Santa Cruz Biotechnology, Inc.

Immunofluorescent Staining. Harvested cells were washed and resuspended in PBS. Cell density was adjusted to ~10$^5$ cells/ml. 0.5 ml aliquots of this cell suspension were centrifuged onto clean glass slides at 800 rpm for 4 min, using a Shandon Cytospin. Immediately after cytocentrifugation, the preparations were fixed in absolute methanol for 30 min at −20° C. and then rinsed in ice-cold acetone for a few seconds. Following three washes with PBS, the preparations were incubated at 37° C. with rabbit anti-HsRad51 antiserum, diluted 1:100 with PBS, in a humidified incubator for 30 min. For some experiments, the slides were simultaneously labeled with rat anti-HsRad52 antiserum or mouse monoclonal antibody. The slides were then washed in PBS another three times for 10 min each and incubated for 30 min with fluorescein-isothiocyanate (FITC)-conjugated anti-rabbit IaG, appropriately diluted with PBS. Rad52, Gadd45, p53, and RNAPII were detected with rhodamine, conjugated anti-rat IgG or anti-mouse IgG+ IgM. After three further washes with PBS, the preparations were counterstained with 1 μg/ml 4,6-diamidino-2-phenylindole (DAPI) in 2×SSC for 5 min. The slides were mounted in 90% glycerol, 0.1 M Tris-HCl, pH 8.0, and 2.3% 1,4-diazobicyclo-2,2,2-octane (DABCO).

For preparation of chromatin fibers, cells were centrifuged onto a glass slide and covered with 50 μl of 50 mM Tris-HCl, pH 8.0, 1 mM EDTA, and 0.1% SDS. The protein-extracted chromatin was mechanically sheared on the slide with the aid of another slide (Heiskanan, et al., (1994) BioTechniques 17, 928–933) and then fixed in methanol/acetone.

Fluorescence In Situ End Labeling (FISEL). FISEL detects cell death (apoptosis) in situ by quantitating DNA strand breaks in individual nuclei. It uses terminal transferase (TdT) to label the 3'-ends in fragmented genomic DNA with biotinylated nucleotide. 100 μl of reaction mix contain 1 μl (25 Units) TdT (Boehringer Mannheim), 20 μl 5×TdT buffer (supplied with the enyzme), 1 μl 0.5 mM biotin-ll-dUTP, 3 μl 0.5 mM dTTP, and 75 μl ddH$_2$O. Cytological preparations are incubated at 37° C. for 1 hr with this reaction mix. Washing the slides for 3×5 min in PBS is sufficient to terminate the reaction. The incorporated biotin-dUTP is detected with rhodarnine-conjugated avidin.

In Situ Labeling of DNA-Replication Synthesis. The base analog BrdU is incorporated in place of thymidine into the DNA of replicating cells. In order to mark cycling cells, 10 μg/ml BrdU were added to the culture medium 30 hrs before cell harvesting. Depending on the cell substrate, this corresponds to one or two population doublings. At the end of the labeling period, slides were prepared as described above. After Rad51-protein staining, the preparations were again fixed in a 3:1 mixture of methanol and acetic acid for several hours at −20° C. Since the anti-BrdU antibody only recognizes BrdU incorporated into chromosomal DNA if the DNA is in the single-stranded form, the slides were denatured in 70% formamide, 2×SSC for 1 min at 80° C. and then dehydrated in an alcohol series. BrdU incorporation was visualized by indirect anti-BrdU antibody staining. First, the preparations were incubated with mouse monoclonal anti-BrdU antibody (Boehringer Mannheim), diluted 1:50 with PBS, for 30 min. The slides were washed with PBS and then incubated with rhodamine-conjugated anti-mouse IgG, diluted 1:20 with PBS, for another 30 min. Only cells with intense BrdU labeling of the entire nucleus were considered BrdU-positive and scored as cycling cells.

Overexpression of HsRad51 Protein in Mammalian Cells. Human kidney cells (line 293, ATCC CRL1573) were stably transformed by plasmid pEG9 15. This plasmid carries the whole coding sequence of the HsRad51 gene inserted in frame with the 5'-end terminal sequence of vector pEB-VHisB (Invitrogen). The resulting cell lines 710 and 717 constitutively express Rad51 protein fused to a T7-tag epitope (Haaf et al., 1995).

Digital Imaging Microscopy. Images were taken with a Zeiss epifluorescence microscope equipped with a thermoelectronically cooled charge coupled device (CCD) camera (Photometries CH250), which was controlled by an Apple Macintosh computer. Gray scale source images were captured separately with filter sets for FITC, rhodamine, and DAPI. Gray scale images were pseudocolored and merged using ONCOR Image and ADOBE Photoshop software. It is worth emphasizing that although a CCD imaging system was used, the immunofluorescent signals described here were clearly visible by eye through the microscope.

Dynamic Nuclear Distribution of Rad51 Protein after DNA, Damage Nuclear foci of mammalian Rad51-recombination protein can be induced significantly after irradiation of cell cultures with Cesium ($^{137}$Cs). Since Western blots have not shown a dramatic net increase in Rad51 protein in irradiated cells, we conclude that DNA damage mainly affects its nuclear distribution (Haaf et al., 1995). To gain insight into the radiation-induced perturbations in nuclear organization and the possible role of Rad51 protein in repair processes, we have analyzed the topological rearrangements of Rad51-protein foci in rat TGR-I fibroblasts that have sustained DNA damage. TGR-I is an immortal rat cell line with a stably diploid karyotype. After $^{137}$Cs irradiation with a dose of 900 red which kills 99% of cells, rat Rad51 protein was visualized in situ using polyclonal antibodies raised against HsRad51. The percentage of cells with cytologically detectable Rad: 1-protein foci started to increase in the first three hours (Table 6). Rad51-positive nuclei contained up to several dozen discrete foci throughout their nucleoplasm. Immunofluorescence staining was largely excluded from the cytoplasm. Many of these nuclear Rad51 foci had a double-dot appearance, typical of paired DNA segments (FIG. 3A).

TABLE 6

Induction of Rad51 Foci after $^{137}$Cs Irradiation of TGR-1 cells and Their Elimination into Micronuclei

| Treatment | Percentage of Cells without Foci | Percentage of Cells with Type I[a] Foci | | Percentage of Cells with Type II[a] Foci | |
|---|---|---|---|---|---|
| | | in Nuclei | in Micro-nuceli | in Nuclei | in Micro-nuclei |
| None | 93% | 6% | 0% | 1% | 0% |
| 3 hrs after 900 rad $^{137}$Cs | 80% | 8% | 0.4% | 11% | 0.6% |
| 16 hrs after 900 rad $^{137}$Cs | 73% | 9% | 8% | 1% | 9% |
| 30 hrs after 900 rad $^{137}$Cs | 72% | 1% | 13% | 1% | 13% |
| 4 days after 900 rad $^{137}$Cs | 90% | 0% | 4% | 0% | 6% |

[a]Type I nuclei and micronuclei show weak to medium HsRad51 immunofluorescence, whereas type II cells show strongly fluorescing foci. 1000 cells were analyzed for each experiment.

When irradiated cells were then cultured for various times to allow repair of induced DNA damage and apoptosis to occur, significant changes in the distribution of Rad51-protein foci were detected. Nuclear foci coalesced into larger clusters with extremely high immunofluorescence intensity after 6–20 furs. Only a few discrete foci remained singly in the nucleoplasm. In a percentage of nuclei linear strings of 5–10 Rad51-protein foci were formed (FIG. 3B). Immediately striking was the somatic association of "homologous" strings of similar length. These strings were always tightly paired at one of their ends. The dynamics of the Rad51-protein foci after induction of DNA damage are clear evidence for a higher-order organization of nuclear structure that accompanies DNA repair and/or programmed cell death.

One to two days after $^{137}$CS irradiation with a lethal dose the coalesced Rad51 clusters showed a highly non-random localization towards the nuclear periphery (FIG. 3C). Finally, the Rad51 structures were excluded into micronuclei. The nucleoplasm was virtually cleared of Rad51 protein and only aggregated Rad51 foci in MN were remaining (FIG. 4; Table 6). Similar to the situation seen earlier in interphase nuclei, many MN displayed paired Rad51 foci and higher-order structures. The highest number of MN (approximately three per cell) as well as the highest number of Rad51-positive MN(approximately 30%) were observed 16 hrs after irradiation (Table 7). However, at each time point analyzed the majority of radiation-induced MN did not show detectable Rad51-protein foci.

TABLE 7

Rad51 Foci in Micronuclei of Different Cell Substrates

| Cell substrate Treatment | Number of Micronuclei in 1000 Cells | Percentage of Rad51-Positive Micronuclei | Percentage of Rad51-Negative Micronuclei |
|---|---|---|---|
| TGR01 | | | |
| None | 93 | 14% | 86% |
| 3 hrs after 900 rad $^{137}$Cs | 279 | 22% | 78% |
| 16 hrs after 900 rad $^{137}$Cs | 2719 | 28% | 72% |
| 4 days after 900 rad $^{137}$Cs | 1040 | 20% | 80% |
| LNL8 | | | |
| None | n.d. | 23% | 77% |
| None XPA | n.d. | 26% | 74% |
| None Teratoma | n.d. | 18% | 82% |
| None 3T3-Swiss | n.d. | 10% | 90% |
| None | 472 | 125% | 88% |

1000 cells were analyzed for each experiment

Segregation of Rad51-Protein Foci into Micronuclei An increased rate of MN is also observed in 5-azadeoxycytidine (5-aza-dC)-treated cell cultures (Guttenbach, et al., (1994) Exp. Cell Res. 211, 127–132; Stopper et al., 1995, supra). This hypomethylating base analog induces inhibition of chromatin condensation, leading to instability of the affected chromosome regions (Haaf, 1995). Its cytotoxic effects are at least partially due to the induction of single- and double-strand breaks in DNA. Like $^{137}$CS irradiation, 5-aza-dC can induce the formation of Rad51-protein foci in nuclei and its elimination into MN. Rat TGR-I and human LNL8 fibroblast cultures treated with non-lethal doses of 5-aza-dC displayed MN with focally concentrated Rad51 protein in 5–10% of their cells (Table 8).

TABLE 8

Induction of Rad51 Foci by 5-Azadeoxycytidine

| Cell type Treatment | Percentage of Cells without Foci | Percentage of Cells with Type I$^a$ Foci | | Percentage of Cells with Type II$^a$ Foci | |
|---|---|---|---|---|---|
| | | in Nuclei | in Micro-nuceli | in Nuclei | in Micro-nuclei |
| TGR-1 | | | | | |
| None | 93% | 6% | 0% | 1% | 0% |
| 5-aza-dC$^b$ | 86% | 5% | 4% | 1% | 4% |
| LNL8 | | | | | |
| None | 92% | 6% | 1% | 1% | 0% |
| 5-aza-dC$^b$ | 89% | 3% | 1% | 2% | 5% |

$^a$Type I nuclei and micronuclei show weak to medium HsRad51 immunofluorescence, whereas type II cells show strongly fluorescing foci. 500 cells were analyzed for each experiment.
$^b$10$^{-5}$ M 5-aza-dC were added to the culture medium 24 hours before cell harvest.

Rapidly dividing cell cultures always exhibit a baseline MN frequency even without exposure to clastogens or aneuploidogens. In five different substrates studied, LNL8, XPA, teratoma, 3T3-Swiss, and TGR-I cells, 10–30% of these spontaneously occurring, non-induced MN exhibited Rad51-protein foci (Table 7). This further links Rad51-protein foci and MN formation.

Rad52 and Other Repair Proteins Are Not Excluded into Micronuclei Studies in yeast (Shinohara et al., 1992, supra; Milne, G., and Weaver, D. (1993). Genes Dev. 7, 1755–1765) and humans (Shen, et al., (1996). J. Biol. Chem. 271, 148–152) have shown physical interaction between Rad51 and Rad52 proteins both in vitro and in vivo. Double immunofluorescence with rabbit anti-Rad51 and rat anti-Rad52 antibodies on $^{137}$CS irradiated TGR-I cells showed that both proteins are enriched in nuclear foci but they do not co-localize. Rad52-protein foci remained in the nucleus throughout the entire time course, while Rad51-protein foci were segregated into MN (data not shown). The same holds true for Gadd45 (data not shown) an inducible DNA-repair protein that is stimulated by p53 (Smith et al., 1994, supra). Biochemical evidence further suggests specific protein-protein association between HsRad51 and p53 (Sturzbecher et al., 1996, supra). However, after anti-p53 antibody staining the Rad51 foci were not particularly enriched with p53 protein (data not shown). In addition, HsRad51 was reported to be associated with a RNA polymerase II (RNAPII) holoenyme (Maldonado et al., 1996, supra). Although RNAPII was immunolocalized in discrete nuclear foci, as reported previously (Bregman et al., 1995, supra), transcription complexes did not coincide with Rad51 foci (data not shown).

Association of Rad51 Protein with DNA Fibers In a few (<1%) cells of irradiated and drug-treated cultures, we observed very elongated Rad51 structures, up to several hundred micrometer in length, that were eliminated from the nuclei. Since these fiber-like structures stained DAPI-positively, they are thought to contain single DNA molecules of several megabases covered with Rad51 (data not shown). Fluorescence in situ end labeling (FISEL) demonstrated that these DNA fibers contain fragmented DNA typical of apoptosis (data not shown). Sometimes the DNA fibers appeared to leak out of the nucleus through holes in the nuclear membrane and condense into micronuclei. In all cell substrates studied, a high percentage of MN displayed genome fragmentation (data not shown).

The association of Rad51 protein with DNA was also visible on experimentally extended chromatin fibers from irradiated cells. SDS lysis and mechanical stretching of nuclear chromatin across the surface of a glass slide can cause complete detachment of DNA loops from the nuclear matrix, producing highly elongated, linear chromatin fibers (Haaf, T., and Ward, D.C. (1994). Hum. Mol. Genet. 3, 629–633.; Heiskanen et al., 1994, supra). Immunofluorescence staining revealed linear strings of Rad51 label on these stretched DNA fibers (data not shown). By comparison with YAC hybridization signals on similar preparations (Haaf and Ward, 1994, supra), the length of the Rad51 fibers was estimated 1–2 Mb.

Rad51-Protein Foci and Apoptosis To determine whether Rad51-positive MN specifically detect exposure to clastogens, analyses were performed in rat TGR-I cells with the aneuploidogen colcemid. This mitotic spindle poison causes lagging of whole chromosomes that are excluded into MN. Surprisingly, when colcemid-treated cells were allowed to recover for 24 hrs in drug-free medium, over 30% of the induced MN contained very brightly fluorescing Rad51 foci (Table 9). Some MN contained rod-like linear structures (data not shown) similar to those observed in Rad51-overexpressing cells. Most of these Rad51-positive MN, 24 hrs after colcemid, did not contain fragmented DNA, as determined by simultaneous FISEL (Table 9). When cells were grown for one or two more days in the absence of the drug, the percentage of Rad51-containing MN decreased dramatically. In addition, the Rad51 protein was no longer concentrated in discrete foci but appeared to disperse throughout the entire MN volume. At the same time most M4N became apoptotic and by FISEL their degraded DNA showed incorporation of fluorescent nucleotides. Thus, we conclude that mitotic arrest after colcemid triggers a cascade that induces the elimination of Rad51 protein into MN and drives apoptotic events. Our results seem to be consistent with the hypothesis that apoptosis is a special form of aberrant mitosis (Ucker, D.S. (1991). New Biologist 3, 103–1009; Shietal., 1994, supra).

Another more classical way for inducing apoptosis in vitro is the exposure of TGR-I cells to the topoisomerase II inhibitor etoposide. After adding etoposide to the culture medium, the percentage of apoptotic cells steadily increased (Table 10). After 36 hrs half of the cells showed genome fragmentation and stained FISEL-positively. The nuclear events of apoptosis were accompanied by the appearance of Rad51 protein in nuclei and MN. These results indicate that different stimuli (e.g., irradiation and DNA-damaging drugs, topoisomerase inhibitors, and aneuploidogens) that condemn cells to apoptosis can induce focal concentration of Rad51 protein and its exclusion into MN.

TABLE 10

Induction of Rad51 Foci and Apoptosis by Etoposide Treatment of TGR-1 Cells

| Treatment | Percentage of Apoptotic Cells[b] | Percentage of Cells without Foci | Percentage of Cells with Type I[a] Foci in Nuclei | Percentage of Cells with Type I[a] Foci in Micronuclei | Percentage of Cells with Type II[a] Foci in Nuclei | Percentage of Cells with Type II[a] Foci in Micronuclei |
|---|---|---|---|---|---|---|
| None | 6% | 93% | 6% | 0% | 1% | 0% |
| 2 hrs after etoposide[c] | n.d. | 92% | 4% | 1% | 1% | 2% |
| 5 hrs after etoposide | n.d | 92% | 3% | 2% | 1% | 2% |
| 12 hrs after etoposide | 17% | 87% | 8% | 2% | 1% | 2% |
| 18 hrs after etoposide | 24% | 79% | 3% | 8% | 1% | 9% |
| 24 hrs after etoposide | 33% | 82% | 2% | 2% | 6% | 8% |
| 36 hrs after etoposide | 47% | 83% | 2% | 5% | 1% | 9% |

[a]Type I nuclei and micronuclei show weak to medium HsRad51 immunofluorescence, whereas type II cells show strongly fluorescing foci. 500 cells were analyzed for each experiment.
[b]Detected by fluorescence in situ end labeling (FISEL+).
[c]Cells were grown in medium containing etoposide for the indicated times.

TABLE 9

Rad51 Foci and Apoptosis in Colcemid-Induced Micronuclei of TGR-1 Cells

| Treatment | Number of micro nuclei in 1000 cells | Rad51−/ FISEL− | Rad51+/ FISEL− | Rad 51+/ FISEL+ | Rad51−/ FISEL+ |
|---|---|---|---|---|---|
| None | 93 | 75% | 12% | 2% | 11% |
| Colcemid[b] | n.d. | 85% | 6% | 0% | 9% |
| 1 day of recovery | 1293 | 54% | 31% | 1% | 14% |
| 2 days of recovery | 1061 | 45% | 9% | 6% | 40% |
| 3 days of recovery | 769 | 43% | 7% | 4% | 46% |

[a]Apoptotic cells show fluorescence in situ end labeling (FISEL+), while cells without genome fragmentation show absence of labeling (FISEL−). "Rad51+" cells with Rad51 foci, "Rad51−" cells without foci.
[b]TGR-1 cells were grown for 24 hrs in medium containing 0.1 μg/ml colcemid to induce micronucleus formation (without inducing DNA damage). 185 of the colcemid-treated cells were arrested at metaphase, 17% showed multinuclei (>10 micronuclei), and 65% had no micronuclei. The cells were then allowed to recover for various times in the absence of the drug. 500 micronuclei were analyzed for each experiment.

Higher-Order Nuclear Organization of Overexpressed Rad51 Protein Human 293 cells were transfected with the HsRad51 gene. The resulting cell lines 710 and 717 constitutively expressed a HsRad51-fusion protein. This overexpressed protein formed brightly fluorescing linear structures inside the nucleus (FIG. 7A). Some nuclei were completely filled with a network of rod-like structures (FIG. 7B). Identical Rad51 structures were observed in transformed rat TGR 928.1–9 cells, stably expressing the HsRad51 protein without a tag epitope (data not shown). This suggests that Rad51 protein is able to assemble into higher-order structures within the highly ordered interphase nucleus. The linear nature of RadS1 structures in overexpressing cells is reminiscent of the strings of Rad51-protein foci after DNA damage and colcemid treatment and in meiotic cells (Haaf et al., 1995).

However, in contrast to the situation after DNA damage, the overexpressed HsRad51 protein is not eliminated into MN. The numbers of Rad51-positive MN were not radically different in Rad51-overexpressing human 717 cells versus in 293 control cells and in rat 928.1–9 overexpressers versus in parental TGR-I cells. This means that Rad51 overexpression alone does not cause apoptosis. In exponentially growing unsynchronized cultures, 14% of both 717 and 293 cells (500 cells were analyzed for each experiment) and 8% of both 928.1–9 and TGR-I cells showed cleavage of the cell's DNA by FISEL. We conclude that the segregation of Rad51 into MN is a specific behavior of apoptotic cells and precedes genome fragmentation.

Cell-Cycle Arrest of Cells with Focally Concentrated Rad51 Protein Simultaneous Rad51-protein immunofluorescence and antibromodeoxyuridine (BrdU) antibody staining demonstrated that nuclei with focally concentrated Rad51 protein do not undergo DNA-replication synthesis (data not shown). BrdU was incorporated into replicating DNA of unsynchronized cell cultures for 30 hrs. Rapidly growing transformed cell lines (293, LNL8, XPA, and XPF) which showed detectable Rad51 immunolabeling in a percentage of nuclei even without induction of DNA damage as well as Rad51 overproducers (928.1–9 and 717) were analyzed. For each experiment, 100 nuclei with prominent Rad51 foci and 100 nuclei without detectable Rad51 foci were stained with fluorescent anti-BrdU antibody. In the widely different substrates tested, 80%-100% of the cells with focally concentrated Rad51 protein were found to be BrdU-staining negative (Table 11). In contrast, 30%–90% of the cells without Rad51 foci from the same cultures showed BrdU incorporation, indicative of cycling cells. The BrdU-substituted DNA was located in discrete replication sites throughout the nucleus as reported previously (Nakayasu, H., and Berezney, R. (1989). J. Cell Biol. 108, 1–11; Fox, et al., (1991) J. Cell Sci. 99, 247–253). This suggests that even without induction of DNA damage the cells with Rad51 foci are arrested during the cell cycle or enter S phase delayed of the Rad51-foci negative cells.

TABLE 11

Induction of Rad51 Foci after $^{137}$Cs Irradiation of TGR-1 cells and Their Elimination into Micronuclei

| Treatment | Percentage of Cells without Foci | Percentage of Cells with Type I[a] Foci | | Percentage of Cells with Type II[a] Foci | |
|---|---|---|---|---|---|
| | | in Nuclei | in Micro-nuceli | in Nuclei | in Micro-nuclei |
| None | 93% | 6% | 0% | 1% | 0% |
| 3 hrs after 900 rad $^{137}$Cs | 80% | 8% | 0.4% | 11% | 0.6% |
| 16 hrs after 900 rad $^{137}$Cs | 73% | 9% | 8% | 1% | 9% |
| 30 hrs after 900 rad $^{137}$Cs | 72% | 1% | 13% | 1% | 13% |
| 4 days after 900 rad $^{137}$Cs | 90% | 0% | 4% | 0% | 6% |

[a]Type I nuclei and micronuclei show weak to medium HsRad51 immunofluorescence, whereas type II cells show strongly fluorescing foci. 1000 cells were analyzed for each experiment.

Rat TGR-I cells are capable of normal physiological withdrawal into the quiescent (Go) phase of the cell cycle as well as resumption of growth following the appropriate stimuli (Prouty, et al., (1993). Oncogene 8, 899–907). In TGR 928.1–9 cells overexpressing a HsRad51 transgene(s), Go arrest upon serum starvation dramatically induced HsRad: 1-protein foci (Table 12). Synchronous re-entry into the cell cycle after feeding reduced the percentage of HsRad51-foci positive cells to very low levels. However, new Go arrest upon contact inhibition following three population doublings increased the number of cells with nuclear Rad51 foci again. We therefore conclude that cells with prominent nuclear Rad51 foci are most likely in Go or G1 phase of the cell cycle.

TABLE 12

Rad51 Foci in Micronuclei of Different Cell Substrates

| Cell substrate Treatment | Number of Micronuclei in 1000 Cells | Percentage of Rad51-Positive Micronuclei | Percentage of Rad51-Negative Micronuclei |
|---|---|---|---|
| TGR01 | | | |
| None | 93 | 14% | 86% |
| 3 hrs after 900 rad$^{137}$Cs | 279 | 22% | 78% |
| 16 hrs after 900 rad$^{137}$Cs | 2719 | 28% | 72% |
| 4 days after 900 rad$^{137}$Cs | 1040 | 20% | 80% |
| LNL8 | | | |
| None | n.d. | 23% | 77% |
| None | n.d. | 26% | 74% |
| XPA | | | |
| None | n.d. | 18% | 82% |
| Teratoma | | | |
| None | n.d. | 10% | 90% |
| 3T3-Swiss | | | |
| None | 472 | 125% | 88% |

1000 cells were analyzed for each experiment

Other references specifically incorporated by reference are Haaf, T. (1995). Pharmac. Ther. 65, 19–46; Haaf, T., and Schmid, M. (1991). Exp. Cell Res. 192, 325–332; and Owaga, et al, (1993) Science 259, 1896–1899

We claim:

1. A method of diagnosing individuals at risk for a disease state that results in aberrant Rad51 foci comprising:
   a) determining a distribution of Rad51 foci in a tissue of an individual; and
   b) comparing said distribution to a distribution of Rad51 foci from a control tissue,
wherein said comparing step indicates whether the individual is at risk for a disease state that results in aberrant Rad51 foci.

2. The method according to claim 1 wherein said disease state is cancer.

3. The method according to claim 1, wherein the extent of aberrant distribution indicates the severity of the disease states.

4. The method according to claim 1, wherein said distribution of Rad51 foci in said tissue of an individual is determined through the use of polyclonal antibodies.

5. The method according to claim 1, wherein said distribution of Rad51 foci in said tissue of an individual is determined through the use of monoclonal antibodies.

6. The method according to claim 4 or 5, wherein said antibodies are raised against eukaryotic Rad51.

7. The method according to claim 6, wherein said eukaryotic Rad51 is mammalian Rad51.

8. The method according to claim 1, wherein said control tissue is diseased tissue.

9. A method of diagnosing individuals at risk for cancer that results in aberrant Rad51 foci comprising
   a) determining a distribution of Rad51 foci in a potential cancerous tissue of an individual; and
   b) comparing said distribution to a distribution of Rad51 foci from a control tissue,
wherein said comparing step indicates whether the individual is at risk for a cancer that results in aberrant Rad51 foci.

10. The method according to claim 9, wherein the cancer is selected from breast cancer and skin cancer.

11. The method according to claim 9, wherein the cancer is breast cancer.

12. The method according to claim 9, wherein the cancer is skin cancer.

13. The method according to claims 12, wherein the skin cancer is xeroderma pigmentosum of types XP-A or XP-F.

14. The method according to claim 9, wherein said control tissue is cancerous tissue.

15. A method of diagnosing individuals at risk for a disease state associated with apoptosis that results in aberrant Rad51 foci, said method comprising:
   a) determining a distribution of Rad51 foci in a tissue of an individual; and
   b) comparing said distribution to a distribution of Rad51 foci from a control tissue, wherein said comparing step indicates whether the individual is at risk for a disease state associated with apoptosis that results in aberrant Rad51 foci.

16. A method for identifying an apoptotic cell comprising:
   a) determining a distribution of Rad51 foci in a first cell; and
   b) comparing said distribution to a distribution of Rad51 foci in a control cell, wherein said comparing step indicates whether the cell is apoptotic.

17. The method according to claim 16, wherein said distribution of Rad51 foci in said first cell is the association of Rad51 with DNA fibers.

18. The method according to claim 16, wherein said distribution of Rad51 foci in said first cell is the association of Rad51 into micronuclei.

* * * * *